United States Patent
Kodama et al.

(10) Patent No.: US 6,472,386 B1
(45) Date of Patent: Oct. 29, 2002

(54) CYCLIC DIAMINE COMPOUND WITH 5-MEMBERED RING GROUPS

(75) Inventors: Tatsuhiko Kodama, Tokyo (JP); Masahiro Tamura, Higashimurayama (JP); Toshiaki Oda, Higashimurayama (JP); Yukiyoshi Yamazaki, Higashimurayama (JP); Masahiro Nishikawa, Higashimurayama (JP); Takeshi Doi, Higashimurayama (JP); Yoshinori Kyotani, Higashiyamato (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/893,682

(22) Filed: Jun. 29, 2001

(51) Int. Cl.⁷ .............................................. A61K 31/551

(52) U.S. Cl. .................. 514/211.08; 544/359; 544/366; 544/369; 540/553

(58) Field of Search ................................ 544/336, 358, 544/359, 366, 367, 369, 370, 371, 372; 540/484, 553, 557, 596, 598; 514/211.01, 211.08, 242.13

(56) References Cited

FOREIGN PATENT DOCUMENTS

| JP | 9-143075 | 6/1997 |
| JP | 10-67656 | 3/1998 |
| JP | 10-147568 | 6/1998 |
| JP | 10-182550 | 7/1998 |
| JP | 11-92382 | 4/1999 |
| JP | 2000-86641 | 3/2000 |
| JP | 2000-509070 | 7/2000 |
| JP | 2000-319277 | 11/2000 |

OTHER PUBLICATIONS

CA:92:181094 abs of Farmaco, Ed. Sci. by Mazzone et al 35(1) pp. 31–40, 1980.*
CA:91:39396 abs of Farmaco, Ed. Sci. by Mazzone et al 34(5) pp. 390–402, 1979.*
CA:73:25460 abs of DE 1958722 May, 1970.*
CA:75:35937 abs of Diss. Phar. Pharmacol. by Lucka–Sobstel et al 23(2) pp. 135–140, 1971.*
CA:85:177365 abs of God. Vissh. Khim.–Tekhnol Inst. Sofia by Natova et al 21(3) pp.177–85 1973.*
CA:114:101940 abs of J Indian Chem. Xoc by Srivastava et al 67(7) pp. 606–607, 1990.*
U.S. patent application Ser. No. 09/893,697, Kodama et al., filed Jun. 29, 2001.
U.S. patent application Ser. No. 09/893,696, Kodama et al., filed Jun. 29, 2001.
U.S. patent application Ser. No. 09/893,681, Kodama et al., filed Jun. 29, 2001.
U.S. patent application Ser. No. 09/893,699, Kodama et al., filed Jun. 29, 2001.

Y. Ohkawara, et al., "In Situ Expression of the Cell Adhesion Molecules in Bronchial Tissues Form Asthmatics with Air Flow Limitation: In Vivo Evidence of VCAM–1/VLA–4 Interaction in Selective Eosinophil Infiltration", *American Journal of Respiratory Cell and Molecular Biology*, 1995, vol. 12, pp.4–12.
A. Sakai, et al., "P–Selectin and Vascular Cell Adhesion Molecule–1 are Focally Expressed in Aortas of Hypercholesterolemic Rabbits Before Intimal Accumulation of Macrophages and T Lymphocytes", *Arteriosclerosis, Thrombosis, and Vascular Biology*, Feb. 1997, vol. 17, No. 2, pp. 310–316.
H. Wakita, et al., "E–Selectin and Vascular Cell Adhesion Molecule–1 as Critical Adhesion Molecules for Infiltration of T Lymphocytes and Eosinophils in Atopic Dermatitis", *Journal of Cutaneous Pathology*, 1994, pp. 33–39.

(List continued on next page.)

Primary Examiner—Jean F. Vollano
(74) Attorney, Agent, or Firm—Oblon, Spivak, McClelland, Maier & Neustadt, P.C.

(57) ABSTRACT

A compound of formula (1):

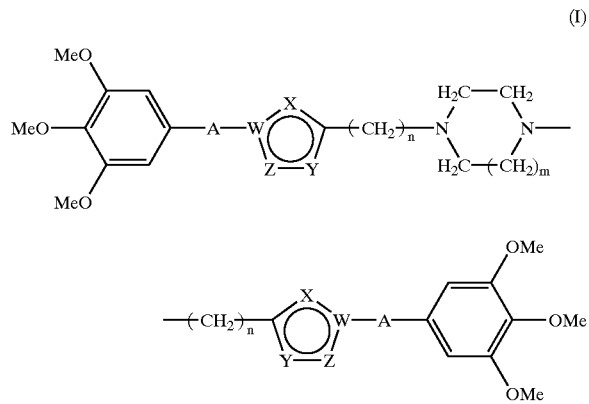

wherein A is a single bond, C≡C, CONH or NHCO; W is a carbon atom or a nitrogen atom; X is CH, a nitrogen atom, an oxygen atom or a sulfur atom; Y is CH, CHR¹, in which R¹ is a hydrogen atom, or a lower alkyl, hydroxy lower alkyl, lower alkoxy-lower-alkyl, aryl, aryl-lower-alkyl or heteroaryl-lower-alkyl group, a nitrogen atom, an oxygen atom, a sulfur atom or NR², in which R² is a hydrogen atom, or a lower alkyl, hydroxy lower alkyl, lower alkoxy-lower-alkyl, aryl, aryl-lower-alkyl or heteroaryl-lower-alkyl group; Z is a nitrogen atom, an oxygen atom, a sulfur atom, CH or NR³, in which R³ is a hydrogen atom, or a lower alkyl, hydroxy lower alkyl, lower alkoxy-lower-alkyl, aryl, aryl-lower-alkyl or heteroaryl-lower-alkyl group; m is 1 or 2; and n is a number of 1 to 5, with the proviso that one or two of W, X, Y and Z are heteroatoms; an acid-addition salt thereof, or a hydrate thereof. The compounds have inhibitory effects on cell adhesion and are useful for prevention or treatment of diseases such as allergy, asthma, rheumatism, arteriosclerosis and inflammation.

14 Claims, No Drawings

OTHER PUBLICATIONS

T. Satoh, et al., "Cyclophosphamide–Induced Blood and Tissue Eosinophilia in Contact Sensitivity: Mechanism of Hapten–Induced Eosinophil Recruitment into the Skin", *European Journal of Immunology,* 1997, vol. 27, pp. 85–91.

P. P. Tak et al., "Expression of Adhesion Molecules in Early Rheumatoid Synovial Tissue", *Clinical Immunology and Immunopathology,* Dec. 1995, vol. 77, No. 3, pp. 236–242.

S. Albelda, et al., "Adhesion Molecules and Inflammatory Injury", *The FASEB Journal,* Reviews, May 1994, vol. 8, pp. 504–512.

T. A. Springer, "Traffic Signals on Endothelium for Lymphocyte Recirculation and Leukocyte Emigration", *Annu. Rev. Physiol.,* 1995, vol. 57, pp. 827–872.

S. A. Michie, et al., "The Roles of α4–Integrins in the Development of Insulin–=Dependent Diabetes Mellitus", *Curr. Top Microbiol. Immunol.,* 1998, vol. 231, pp. 65–83.

N. Ebihara, et al., "Anti VLA–4 Monoclonal Antibody Inhibits Eosinophil Infiltration in Allergic Conjunctivitis Model of Guinea Pig", *Current Eye Research,* 1999, vol. 19, No. 1, pp. 20–25.

S. M. Whitcup, et al., "Blocking ICAM–1 (CD54) and LFA–1 (CD11a) Inhibits Experimental Allergic Conjunctivitis", *Clinical Immunology,* Nov. 1999, vol. 93, No. 2, pp. 107–113.

A. Soriano, et al., "VCAM–1, But Not ICAM–1 or MAdCAM–1, Immunoblockade Ameliorates DSS–Induced Colitis in Mice", *Laboratory Investigation,* Oct. 2000, vol. 80, No. 10, pp. 1541–1551.

A. Zeidler, et al., "Therapeutic Effects of Antibodies Against Adhesion Molecules in Murine Collagen Type II–Induced Arthritis", *Autoimmunity,* 1995, vol. 21, pp. 245–252.

F. Bendjelloul, et al., "Intercellular Adhesion Molecule–1 (ICAM–1) Deficiency Protects Mice Against Severe Forms of Experimentally Induced Colitis", *Clinical and Experimental Immunology,* 2000, vol. 119, pp. 57–63.

W. W. Wolyniec, et al., "Reduction of Antigen–Induced Airway Hyperreactivity and Eosinophilia in ICAM–1–Deficient Mice", *American Journal of Respiratory Cell and Molecular Biology,* 1998, vol. 18, pp. 777–785.

D. C. Bullard, et al., "Reduced Susceptibility to Collagen–Induced Arthritis in Mice Deficient in Intercellular Adhesion Molecule–1[1]", *The Journal of Immunology,* 1996, vol. 157, pp. 3153–3158.

D. H. Boschelli, et al., "Inhibition of E–Selectin–, ICAM–1–, and VCAM–1–Mediated Cell Adhesion by Benzo[b]Thiophene–, Benzofuran–, Indole–, and Naphthalene–2–Carboxamides: Identification of PD 144795 as an Antiinflammatory Agent", *Journal of Medicinal Chemistry,* 1995, vol. 38, No. 22, pp. 4597–4614.

* cited by examiner

CYCLIC DIAMINE COMPOUND WITH 5-MEMBERED RING GROUPS

BACKGROUND OF THE INVENTION

1. Field of the Invention

The present invention relates to novel cyclic diamine compounds which have inhibitory effects on both cell adhesion and cell infiltration and are useful as anti-asthmatic agents, anti-allergic agents, anti-rheumatic agents, anti-arteriosclerotic agents, anti-inflammatory agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am. J. Respir. Cell Mol. Biol., 12, 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita H. et al, J. Cutan. Pathol., 21, 33–39 (1994)) or contact dermatitis (Satoh, T. et al., Eur. J. Immunol., 27, 85–91 (1997)), and infiltration of various leukocytes into rheumatoid synovial tissue (Tak, PP. et al., Clin. Immunol. Immunopathol., 77, 236–242 (1995)), have been reported.

Infiltration of these leukocytes is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57, 827–872 (1995)). In adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)), and a relationship between the disorder state and aberrant expression of the cell adhesion molecules is noted.

Accordingly, an agent capable of inhibiting cell adhesion can be useful as an agent for preventing and treating allergic diseases, such as bronchial asthma, dermatitis, rhinitis and conjunctivitis; autoimmune diseases such as rheumatoid arthritis, nephritis, inflammatory bowel diseases, diabetes and arteriosclerosis; and chronic inflammatory diseases. In fact, it has been reported that antibodies against adhesion molecules on leukocytes such as LFA-1, Mac-1 and VLA-4 or antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231, 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in a mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, D C. et al., J. Immunol., 157, 3153–3158 (1996)).

However, it is difficult to develop antibody-based drugs because they are polypeptides and so oral administration is a problem. Moreover, possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, D H. et al., J. Med. Chem., 38, 4597–4614 (1995)), naphthalene derivatives (Japanese Patent Application Laid-Open No. 10–147568), hydroxybenzoic acid derivatives (Japanese Patent Application Laid-Open No. 10–182550), lignans (Japanese Patent Application Laid-Open No. 10–67656), 2-substituted benzothiazole derivatives (Japanese Patent Application Laid-Open No. 2000-086641 through PCT route), condensed pyrazine compounds (Japanese Patent Application Laid-Open No. 2000-319277 through PCT route), 2,6-dialkyl-4-silylphenol (Japanese Patent Application Laid-Open Re-Publication No. 2000-509070 through PCT route) and the like. However, the goal has not often been sufficiently achieved under the circumstances. Cyclic diamine compounds described in Japanese Patent Application Laid-Open Nos. 9-143075 and 11-92382 do not exhibit a sufficient inhibitory effect on cell adhesion, and so there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects and anti-inflammatory effects.

With the foregoing circumstances in mind, the present inventors carried out an extensive investigation to find a substance which inhibits cell adhesion and cell infiltration. As a result, we found that compounds represented by the general formula (1) have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents.

The present invention provides a cyclic diamine compound represented by the following general formula (1):

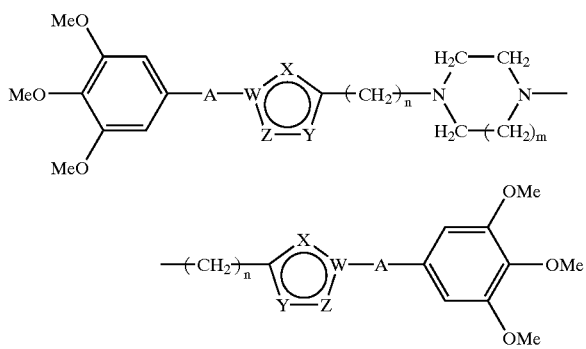

wherein A is a single bond, C≡C, CONH or NHCO; W is a carbon atom or a nitrogen atom; X is CH, a nitrogen atom, an oxygen atom or a sulfur atom; Y is CH, $CHR^1$, in which $R^1$ is a hydrogen atom, or a lower alkyl, hydroxy lower alkyl, lower alkoxy-lower-alkyl, aryl, aryl-lower-alkyl or heteroaryl-lower-alkyl group, a nitrogen atom, an oxygen atom, a sulfur atom or $NR^2$, in which $R^2$ is a hydrogen atom, or a lower alkyl, hydroxy lower alkyl, lower alkoxy-lower-alkyl, aryl, aryl-lower-alkyl or heteroaryl-lower-alkyl group; Z is a nitrogen atom, an oxygen atom, a sulfur atom, CH or $NR^3$, in which $R^3$ is a hydrogen atom, or a lower alkyl, hydroxy lower alkyl, lower alkoxy-lower-alkyl, aryl, aryl-lower-alkyl or heteroaryl-lower-alkyl group; m is 1 or 2; and n is a number of 1 to 5, with the proviso that one or two of W, X, Y and Z are heteroatoms;

an acid-addition salt thereof, or a hydrate thereof.

According to the present invention, there is also provided a medicine comprising the compound represented by the general formula (1), a acid-addition salt thereof, or a hydrate thereof as an active ingredient.

According to the present invention, there is further provided a medicinal composition comprising the compound represented by the general formula (1), the acid-addition salt thereof, or the hydrate thereof and a pharmaceutically acceptable carrier.

According to the present invention, there is still further provided a method for treating a disease caused by cell adhesion and/or cell infiltration, which comprises administering an effective amount of the compound represented by the general formula (1), a acid-addition salt thereof, or a hydrate thereof to a patient who requires such treatment.

DETAILED DESCRIPTION OF THE PREFERRED EMBODIMENTS

The lower alkyl groups represented by $R^1$, $R^2$ and $R^3$ in general formula (1) include $C_1$–$C_6$-alkyl groups, for example, methyl, ethyl, n-propyl, isopropyl, n-butyl, isobutyl, tert-butyl, pentyl and hexyl groups, with methyl, ethyl, n-propyl and isopropyl groups being particularly preferred. The hydroxy lower alkyl groups include hydroxy-$C_2$–$C_6$-alkyl groups, for example, 2-hydroxyethyl, 2-hydroxy-1-methylethyl, 2-hydroxy-1,1-dimethylethyl, 3-hydroxypropyl, 3-hydroxy-2-methylpropyl, 4-hydroxybutyl, 5-hydroxypentyl and 6-hydroxyhexyl groups, with 2-hydroxyethyl, 2-hydroxy-1-methylethyl, 2-hydroxy-1,1-dimethylethyl and 3-hydroxypropyl groups being particularly preferred. The lower alkoxy-lower-alkyl groups include $C_1$–$C_6$-alkoxy-$C_1$–$C_6$-alkyl groups, for example, 2-methoxyethyl, 2-methoxy-1-methylethyl, 2-methoxy-1,1-dimethylethyl, 3-methoxypropyl, 3-methoxy-2-methylpropyl, 4-methoxybutyl, 5-methoxypentyl, 6-methoxyhexyl, 2-ethoxyethyl, 2-ethoxy-1-methylethyl, 2-ethoxy-1,1-dimethylethyl, 3-ethoxypropyl, 3-ethoxy-2-methylpropyl, 4-ethoxybutyl, 5-ethoxypentyl, 6-ethoxyhexyl, 2-propoxy-ethyl, 2-propoxy-1-methylethyl, 2-propoxy-1,1-dimethyl-ethyl, 3-propoxypropyl, 3-propoxy-2-methylpropyl, 4-propoxybutyl, 5-propoxypentyl, 6-methoxyhexyl, 2-butoxyethyl, 2-butoxy-1-methylethyl, 2-butoxy-1,1-dimethylethyl, 3-butoxypropyl, 3-butoxy-2-methylpropyl, 4-butoxybutyl, 5-butoxypentyl, 6-butoxyhexyl, 2-pentyloxy-ethyl, 2-pentyloxy-1-methylethyl, 2-pentyloxy-1,1-dimethylethyl, 3-pentyloxypropyl, 3-pentyloxy-2-methyl-propyl, 4-pentyloxybutyl, 5-pentyloxypentyl, 6-pentyloxy-hexyl, 2-hexyloxyethyl, 2-hexyloxy-1-methylethyl, 2-hexyloxy-1,1-dimethylethyl, 3-hexyloxypropyl, 3-hexyloxy-2-methylpropyl, 4-hexyloxybutyl, 5-hexyloxypentyl and 6-hexyloxyhexyl groups, with 2-methoxyethyl, 2-methoxy-1-methylethyl, 2-methoxy-1,1-dimethylethyl, 3-methoxypropyl, 2-ethoxyethyl, 2-ethoxy-1-methylethyl, 2-ethoxy-1,1-dimethylethyl, 3-ethoxypropyl, 2-propoxyethyl, 2-propoxy-1-methylethyl, 2-propoxy-1,1-dimethylethyl and 3-propoxypropyl groups being particularly preferred. The aryl groups include $C_6$–$C_{10}$-aryl groups, for example, a phenyl group. The aryl-lower-alkyl groups include $C_6$–$C_{10}$-aryl-$C_1$–$C_6$-alkyl groups. In particular, phenyl-$C_1$–$C_6$-alkyl groups such as phenethyl and benzyl groups are preferred.

The heteroaryl-lower-alkyl groups include pyridyl-$C_1$–$C_6$-alkyl groups, for example, a pyridylmethyl group.

In general formula (1), the heterocycle constituting the moiety

is a 5-membered heterocycle having one or two atoms selected from nitrogen, oxygen and sulfur atoms, and specific examples thereof include heterocycles selected from thiazole, oxazole, imidazole, pyrazole, isothiazole, isoxazole, pyrrole, thiophene and furan. Of these, thiazole, oxazole, imidazole, isoxazole and thiophene are particularly preferred.

The value of n is from 1 to 5, with a number of 1 to 3 being preferred.

No particular limitation is imposed on the acid-addition salts of the compounds (1) according to the invention as long as they are pharmaceutically acceptable salts. Examples include the acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds of formula (1) may be present in the form of solvates typified by hydrates, and the solvates are embraced in the present invention.

The compound (1) according to the present invention can be prepared in accordance with, for example, the following reaction formula:

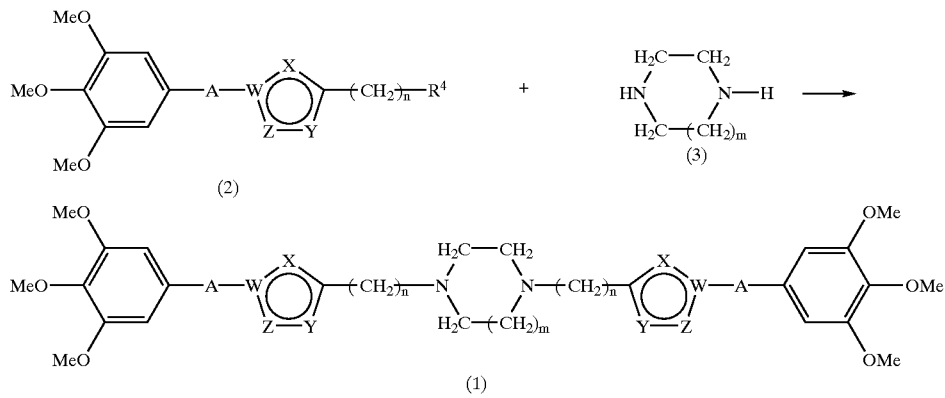

(2) + (3) →

(1)

wherein $R^4$ is a halogen atom, or an alkylsulfonyloxy or arylsulfonyloxy group, and A, W, X, Y, Z, m and n have the same meanings as defined above.

More specifically, compounds (1) are obtained by condensing a compound (2) with a cyclic diamine (3). As the halogen atom in the general formula (2), a chlorine or bromine atom is preferred. As the alkylsulfonyloxy group, a methanesulfonyloxy group is preferred. As the arylsulfonyloxy group, a p-toluenesulfonyloxy group is preferred.

The condensation reaction of compound (2) with cyclic diamine (3) is conducted by stirring the reactants at room temperature to 100° C., preferably room temperature for 1 hour to several days in the presence of a base such as potassium carbonate in a solvent such as N,N-dimethylformamide (DMF), dimethyl sulfoxide (DMSO) or acetonitrile. In order to provide a compound in which $R^2$ and/or $R^3$ is a hydrogen atom, it is preferred that a compound (2), in which $R^2$ and/or $R^3$ is a protecting group such as a methoxymethyl group, be condensed with the cyclic diamine (3), and deprotection of the protecting group be then conducted to obtain the intended compound (1).

The compound (2) which is a raw material can be prepared in accordance with, for example, the following reaction formula:

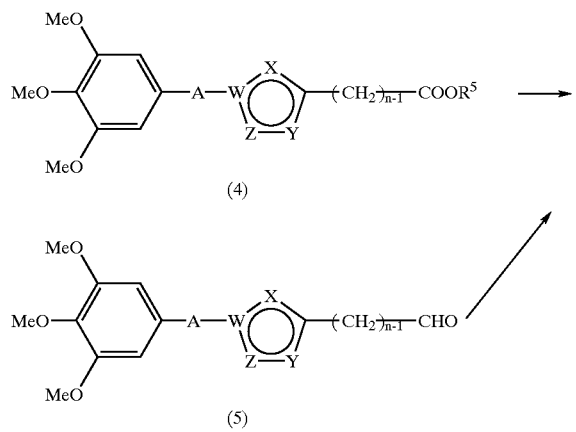

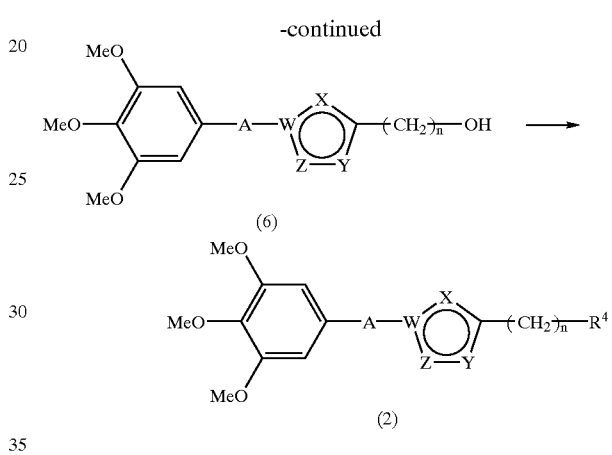

wherein $R^5$ is a hydrogen atom or an alkyl group, and A, W, X, Y, Z, n and $R^4$ have the same meanings as defined above.

More specifically, a carboxy derivative (4) or an aldehyde (5) is reduced to obtain an alcohol (6). The alcohol is reacted with a halogenating agent, alkylsulfonyl chloride, arylsulfonyl chloride or the like, thereby obtaining the compound (2). The reduction reaction of the carboxy derivative (4) or the aldehyde (5) is preferably conducted by, for example, causing the carboxy derivative (4) or the aldehyde (5) to react at −20° C. to room temperature, preferably 0° C. for several seconds to several hours, preferably 30 minutes using a reducing agent such as lithium aluminum hydride in tetrahydrofuran (THF). The reaction of the alcohol (6) with thionyl chloride, or methanesulfonyl chloride or the like is preferably conducted by stirring the reactants at −20° C. to room temperature, preferably 0° C. for 1 hour to several days, preferably 5 hours in a solvent such as chloroform, dichloromethane, ethyl acetate, ether, THF or dioxane for thionyl chloride or in the presence of a base such as triethylamine or pyridine in a solvent such as chloroform, dichloromethane, ethyl acetate, ether, THF, dioxane or pyridine for methanesulfonyl chloride or the like.

The compounds (1) according to the present invention are obtained by the above-described process and may further be purified by using an ordinary purification means such as recrystallization or column chromatography as needed. As needed, the compounds may also be converted into the desired salts or solvates by known methods. When the compounds (1) have an asymmetric carbon atom, the present invention includes any configurational isomers.

The compounds (1) according to the present invention, or salts or solvates thereof thus obtained have an excellent inhibitory effect of cell adhesion as demonstrated in the Examples, which will be described subsequently, and are useful as medicines for treatment or prevention of diseases of animals including humans, such as asthma, allergy, rheumatism, arteriosclerosis and inflammation.

The medicine according to the present invention comprises a compound (1), a salt thereof, or a solvate thereof as an active ingredient. The form of administration may be suitably selected as necessary for the therapeutic application intended without any particular limitation and any of, for example, oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, a disintegrator, a lubricant, a colorant, a taste corrigent, a smell corrigent and the like are added to compound (1), and the resulting composition can be formulated into tablets, coated tablets, granules, powders, capsules, etc. in accordance with methods known in the art.

As such additives described above, any additives may be used which are generally used in the pharmaceutical field. Examples include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1), and the resulting composition can be formulated into internal liquid preparations, syrup preparations, elixirs, etc. in accordance with methods known in the art. In this case, vanillin as the taste corrigent, may be used. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to the compound (1) according to the present invention, and the resultant composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with known methods. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by Examples. However, the invention is not limited to these examples.

PREPARATION EXAMPLE 1

Synthesis of 3,4,5-Trimethoxybenzothioamide 3,4,5-Trimethoxybenzamide (5.0 g) and 2,4-bis(4-methoxyphenyl)-1,3-dithia-2,4-diphosphetane-2,4-disulfide (5.24 g) were added to toluene, and the mixture was stirred at 70° C. After 5 hours, the reaction mixture was cooled back to room temperature, diluted with ethyl acetate, washed with saturated brine, dried over anhydrous sodium sulfate, and concentrated under reduced pressure. The residue was then purified by column chromatography on silica gel (hexane:ethyl acetate=1:1 to 1:2) to obtain yellow crystals, and the crystals were further recrystallized from ethyl acetate-hexane to obtain the title compound.

Yield: 4.01 g (75%). $^1$H-NMR (400 MHz, CDCl$_3$) δ: 3.88 (s, 3H), 3.90 (s, 6H), 7.11 (s, 2H).

PREPARATION EXAMPLE 2

Synthesis of Ethyl 2-(3,4,5-Trimethoxyphenyl) thiazole-4-carboxylate 3,4,5-Trimethoxybenzothioamide (2.5 g) and 90% ethyl bromopyruvate (2.62 g) were added to ethanol (20 mL), and the mixture was stirred at 80° C. for 1 hour. The reaction mixture was concentrated under reduced pressure, and the residue was diluted with ethyl acetate, washed with a saturated aqueous solution of sodium hydrogencarbonate, water and saturated brine, dried over anhydrous sodium sulfate and concentrated under reduced pressure. The residue was then purified by column chromatography on silica gel (hexane:ethyl acetate=1:1) and further recrystallized from ethyl acetate-hexane to obtain the title compound.

Yield: 2.94 g (83%). $^1$H-NMR (400 MHz, CDCl$_3$) δ: 1.50 (t, 3H, J=7.0 Hz), 3.96 (s, 3H), 4.03 (s, 6H), 4.55 (q, 2H, J=7.1 Hz), 7.54 (s, 2H), 8.22 (s, 1H).

PREPARATION EXAMPLE 3

Synthesis of 4-Hydroxymethyl-2-(3,4,5-trimethoxyphenyl)-thiazole

Ethyl 2-(3,4,5-trimethoxyphenyl)thiazole-4-carboxylate (6.9 g) was dissolved in THF (100 mL), and to the solution lithium aluminum hydride (810 mg) was added under an argon atmosphere, and the mixture was stirred at 0° C. for 1 hour. After a small amount of water and then sodium sulfate were added to the reaction mixture, the reaction mixture was filtered through celite, and the filtrate was concentrated under reduced pressure. The resultant crude crystals were recrystallized from ethyl acetate-hexane to obtain the title compound.

Yield: 5.69 g (95%). $^1$H-NMR (400 MHz, CDCl$_3$) δ: 1.63 (br, 1H), 3.89 (s, 3H), 3.94 (s, 6H), 4.82 (s, 2H), 6.83 (s, 2H), 7.26 (s, 1H).

PREPARATION EXAMPLE 4

Synthesis of 4-Chloromethyl-2-(3,4,5-trimethoxyphenyl)-thiazole

4-Hydroxymethyl-2-(3,4,5-trimethoxyphenyl)thiazole (2.0 g) was dissolved in dichloromethane (60 mL), and to the solution thionyl chloride (1.1 g) was added at 0° C. After 30 minutes, the mixture was warmed to room temperature and stirred for 4 hours. The reaction mixture was washed with water and saturated brine and dried over anhydrous sodium sulfate. After concentrating the reaction mixture under reduced pressure, the resultant crude crystals were recrystallized from chloroform-hexane to obtain the title compound.

Yield: 1.97 g (93%). $^1$H-NMR (400 MHz, CDCl$_3$) δ: 3.89 (s, 3H), 3.94 (s, 6H), 4.73 (s, 2H), 7.16 (s, 2H), 7.28 (s, 1H).

EXAMPLE 1

Synthesis of N,N'-bis[[2-(3,4,5-Trimethoxyphenyl) thiazol-4-yl]methyl]piperazine

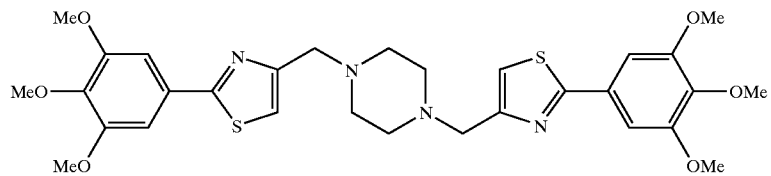

4-Chloromethyl-2-(3,4,5-trimethoxyphenyl)thiazole (240 mg) and piperazine (34 mg) were dissolved in DMF (3 mL), potassium carbonate (166 mL) and potassium iodide (166 mg) were added to the solution, and the mixture was stirred at room temperature for 5 hours. After concentrating the reaction mixture under reduced pressure, chloroform was added to the residue, and the mixture was washed with water and saturated brine, dried over anhydrous magnesium sulfate and then concentrated under reduced pressure. The residue was purified by column chromatography on silica gel (chloroform:methanol=40:1) to obtain the title compound as a free base.

Yield: 79 mg (33%). $^1$H-NMR (400 MHz, CDCl$_3$) δ: 2.67 (s, 8H), 3.76 (s, 4H), 3.88 (s, 6H), 3.94 (s, 12H), 7.12 (s, 2H), 7.16 (s, 4H). m/z (EI): 685 [M$^+$].

EXAMPLE 2

Synthesis of N,N'-bis[[2-(3,4,5-Trimethoxyphenyl) thiazol-4-yl]methyl]homopiperazine

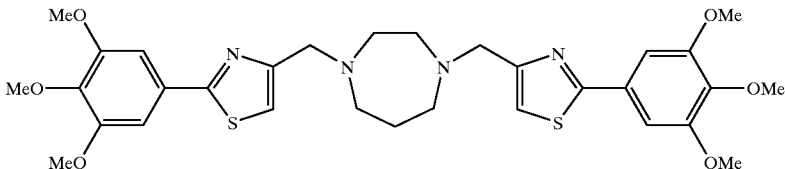

4-Chloromethyl-2-(3,4,5-trimethoxyphenyl)thiazole (198 mg) and homopiperazine (30 mg) were reacted in the same manner in Example 1 to obtain the title compound as a free base.

Yield: 108 mg (58%). $^1$H-NMR (400 MHz, CDCl$_3$) δ: 1.90–1.97 (m, 2H), 2.92–2.95 (m, 8H), 3.89 (s, 6H), 3.94 (s, 16H), 7.16 (s, 4H), 7.21 (s, 2H). m/z (EI): 699 [M$^+$].

PREPARATION EXAMPLE 5

Synthesis of Methyl 2-(3,4,5-Trimethoxyphenyl) thiazole-4-acetate 3,4,5-Trimethoxybenzothioamide (1.0 g) and methyl 4-bromoacetoacetate (858 mg)) were reacted in the same manner in Preparation Example 2 to obtain the title compound.

Yield: 1.16 g (82%). $^1$H-NMR (400 MHz, CDCl$_3$) δ: 3.75 (s, 3H), 3.89 (s, 3H), 3.90 (s, 2H), 3.94 (s, 6H), 7.15 (s, 2H), 7.18 (s, 1H).

PREPARATION EXAMPLE 6

Synthesis of 4-(2-Hydroxyethyl)-2-(3,4,5-trimethoxyphenyl)thiazole

Methyl 2-(3,4,5-trimethoxyphenyl)thiazole-4-acetate (5.0 g) treated in the same manner as in Preparation Example 3 to obtain the title compound.

Yield: 2.64 g (58%). $^1$H-NMR (400 MHz, CDCl$_3$) δ: 1.57 (s, 1H), 3.04 (t, 2H, J=5.6 Hz), 3.89 (s, 3H), 3.94 (s, 6H), 3.99 (t, 2H, J=5.7 Hz), 6.97 (s, 1H), 7.14 (s, 2H).

PREPARATION EXAMPLE 7

Synthesis of 4-(2-Methanesulfonyloxyethyl)-2-(3,4, 5-trimethoxyphenyl)thiazole 4-(2-Hydroxyethyl)-2-(3,4,5-trimethoxyphenyl)-thiazole (1.60 g) was dissolved in pyridine (15 mL), and to the solution methanesulfonyl chloride (807 mg) was added at 0° C., and the mixture was stirred for 1.5 hours. The reaction mixture was diluted with ethyl acetate, washed with 2 M hydrochloric acid, water and saturated brine and dried over anhydrous sodium sulfate. After concentrating the reaction mixture under reduced pressure, the residue was purified by column chromatography on silica gel (ethyl acetate) to obtain the title compound.

Yield: 2.09 g (theoretical amount). ¹H-NMR (400 MHz, CDCl₃) δ: 2.93 (s, 3H), 3.25 (t, 2H, J=6.2 Hz), 3.89 (s, 3H), 3.95 (s, 6H), 4.64 (t, 2H, J=6.5 Hz), 7.05 (s, 1H), 7.15 (s, 2H).

EXAMPLE 3

Synthesis of N,N'-bis[2-[2-(3,4,5-Trimethoxyphenyl)-thiazol-4-yl]ethyl]piperazine

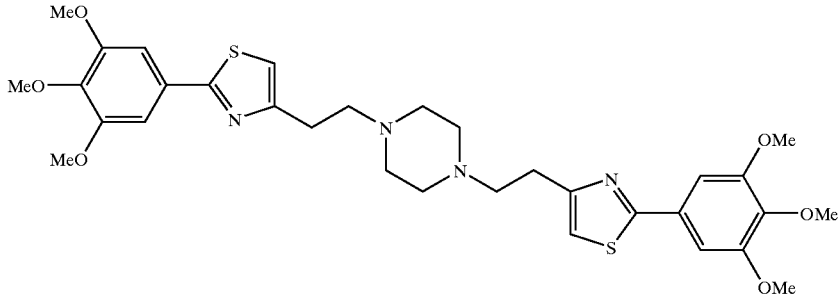

4-(2-Methanesulfonyloxyethyl)-2-(3,4,5-trimethoxyphenyl)thiazole (164 mg) and piperazine (17 mg) were reacted in the same manner in Example 1 to obtain the title compound as a free base.

Yield: 123 mg (96%). ¹H-NMR (400 MHz, CDCl₃) δ: 2.64 (br, 8H), 2.82 (t, 4H, J=7.8 Hz), 3.04 (t, 4H, J=7.8 Hz), 3.89 (s, 6H), 3.95 (s, 12H), 6.96 (s, 2H), 7.16 (s, 4H). m/z (EI): 713 [M⁺].

EXAMPLE 4

Synthesis of N,N'-bis[2-[2-(3,4,5-Trimethoxyphenyl)-thiazol-4-yl]ethyl] homopiperazine

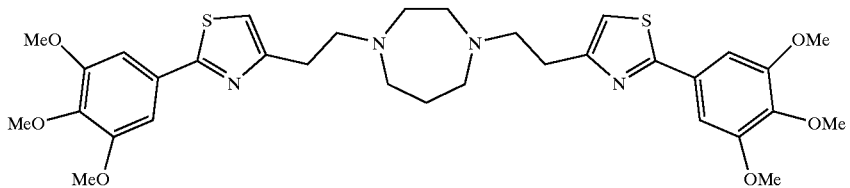

4-(2-Methanesulfonyloxyethyl)-2-(3,4,5-trimethoxyphenyl)thiazole (250mg) and homopiperazine (30mg) were reacted in the same manner in Example 1 to obtain the title compound as a free base.

Yield: 127 mg (65%). ¹H-NMR (400 MHz, CDCl₃) δ: 1.90–1.96 (m, 2H), 2.88–2.91 (m, 8H), 2.98–3.07 (m, 8H), 3.89 (s, 6H), 3.94 (s, 12H), 6.96 (s, 2H), 7.15 (s, 4H). m/z (EI): 727 [M⁺].

PREPARATION EXAMPLE 8

Synthesis of 2-(3,4,5-Trimethoxyphenyl)thiazole-4-carboaldehyde

4-Hydroxymethyl-2-(3,4,5-trimethoxyphenyl)thiazole (1.53 g) was dissolved in a mixed solvent of DMSO (5 mL) and triethylamine (2.3 mL), and sulfur trioxide pyridine complex (98%, 3.09 g) was added portionwise to the solution at room temperature. After 1 hour, the reaction mixture was diluted with ethyl acetate, washed with water and saturated brine and dried over anhydrous sodium sulfate. After concentrating the reaction mixture under reduced pressure, the residue was purified by column chromatography on silica gel (hexane:ethyl acetate=2:1 to 1:2) to obtain the title compound.

Yield: 942 mg (62%). ¹H-NMR (400 MHz, CDCl₃) δ: 3.91 (s, 3H), 3.96 (s, 6H), 7.22 (s, 2H), 8.15 (s, 1H), 10.08 (s, 1H).

PREPARATION EXAMPLE 9

Synthesis of Ethyl 3-[2-(3,4,5-Trimethoxyphenyl) thiazol-4-yl]propenoate

THF (5 mL) was added to sodium hydride (55% dispersion in mineral oil, 162 mg) under an argon atmosphere, and a solution of ethyl diethylphosphonoacetate (832 mg) in THF (2 mL) was added dropwise to the mixture at −10° C. After 30 minutes, a solution of 2-(3,4,5-trimethoxyphenyl) thiazole-4-carboaldehyde (942 mg) in THF (8 mL) was slowly added to the resultant mixture, and the mixture was warmed to room temperature over 30 minutes and then stirred for 2 hours. The reaction mixture was diluted with ethyl acetate, washed with a saturated aqueous solution of sodium hydrogencarbonate, water and saturated brine, dried over anhydrous sodium sulfate. After concentrating the reaction mixture under reduced pressure, the resultant crude crystals were recrystallized from ethyl acetate-hexane to obtain the title compound.

Yield: 997 mg (85%). ¹H-NMR (400 MHz, CDCl₃) δ: 1.35 (t, 3H, J=7.1 Hz), 3.90 (s, 3H), 3.96 (s, 6H), 4.35 (q, 2H, J=7.2 Hz), 6.88 (d, 1H, J=5.0 Hz), 7.21 (s, 2H), 7.39 (s, 1H), 7.61 (d, 1H, J=5.4 Hz).

PREPARATION EXAMPLE 10

Synthesis of Ethyl 3-[2-(3,4,5-Trimethoxyphenyl) thiazol-4-yl]propionate

Ethyl 3-[2-(3,4,5-trimethoxyphenyl)thiazol-4-yl] propenoate (1.65 g) was suspended in methanol (20 mL), 10% palladium on carbon (800 mg) was added to the suspension under an argon atmosphere, and the mixture was stirred at room temperature under a hydrogen amosphere. The reaction mixture was filtered, the filtrate was concentrated, and the residue was purified by column chromatography on silica gel (hexane:ethyl acetate=3:1 to 1:1) to obtain the title compound.

Yield: 1.54 g (93%). $^1$H-NMR (400 MHz, CDCl$_3$) δ: 1.25 (t, 3H, J=7.1 Hz), 2.79 (t, 2H, J=7.5 Hz), 3.13 (t, 2H, J=7.4 Hz), 3.89 (s, 3H), 3.94 (s, 6H), 4.16 (q, 2H, J=7.2 Hz), 6.92 (s, 1H), 7.15 (s, 2H).

reacted in the same manner in Example 1 to obtain the title compound as a free base.

Yield: 44 mg (17%). $^1$H-NMR (400 MHz, CDCl$_3$) δ: 1.96–2.02 (m, 4H), 2.46 (t, 4H, J=7.6 Hz), 2.56 (br, 8H), 2.83 (t, 4H, J=7.6 Hz), 3.88 (s, 6H), 3.94 (s, 12H), 6.87 (s, 2H), 7.15 (s, 4H). m/z (EI): 741 [M$^+$].

EXAMPLE 6

Synthesis of N,N'-bis[3-(2-(3,4,5-Trimethoxyphenyl)-thiazol-4-yl)propyl]homopiperazine

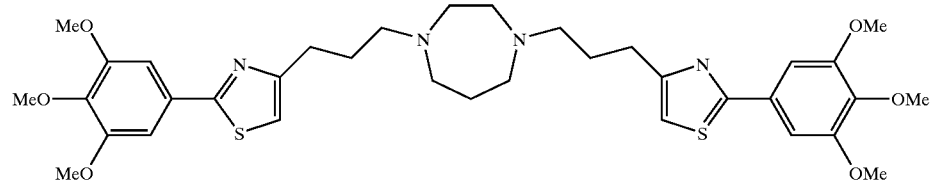

PREPARATION EXAMPLE 11

Synthesis of 4-(3-Hydroxypropyl)-2-(3,4,5-trimethoxy-phenyl)thiazole

Ethyl 3-[2-(3,4,5-trimethoxyphenyl)thiazol-4-yl]propionate (1.65 g) was treated in the same manner as in Preparation Example 3 to obtain a crude product of the title compound.

Yield: 1.5g (containing impurities). $^1$H-NMR (400 MHz, CDCl$_3$) δ: 1.95–2.04 (m, 2H), 2.94 (t, 2H, J=6.8 Hz), 3.29 (br, 1H), 3.75 (t, 2H, J=5.1 Hz), 3.89 (s, 3H), 3.94 (s, 6H), 6.90 (s, 1H), 7.13 (s, 2H).

PREPARATION EXAMPLE 12

Synthesis of 4-(3-Methanesulfonyloxypropyl)-2-(3,4,5-trimethoxyphenyl)thiazole 4-(3-Hydroxypropyl)-2-(3,4,5-trimethoxyphenyl)-thiazole (1.5 g) was reacted in the same manner as in Preparation Example 7 to obtain the title compound.

Yield: 1.37 g (75%). $^1$H-NMR (400 MHz, CDCl$_3$) δ: 2.20–2.27 (m, 2H), 2.95 (t, 2H, J=7.2 Hz), 3.03 (s, 3H), 3.89 (s, 3H), 3.95 (s, 6H), 4.34 (t, 2H, J=6.2 Hz), 6.94 (s, 1H), 7.16 (s, 2H).

EXAMPLE 5

Synthesis of N,N'-bis[3-[2-(3,4,5-Trimethoxyphenyl)-thiazol-4-yl]propyl]piperazine

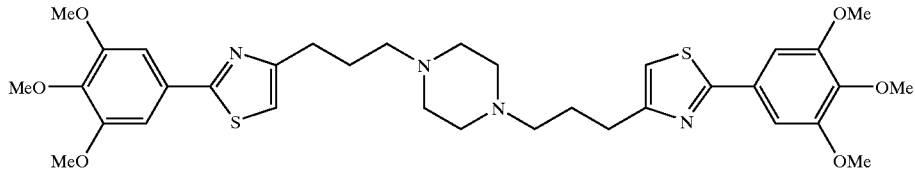

4-(3-Methanesulfonyloxypropyl)-2-(3,4,5-trimethoxy-phenyl)thiazole (310 mg) and piperazine (34 mg) were 4-(3-Methanesulfonyloxypropyl)-2-(3,4,5-trimethoxy-phenyl)thiazole (152 mg) and homopiperazine (20 mg) were reacted in the same manner in Example 1 to obtain the title compound as a free base.

Yield: 56 mg (42%). $^1$H-NMR (400 MHz, CDCl$_3$) δ: 2.00–2.07 (m, 6H), 2.71 (t, 4H, J=7.5 Hz), 2.83 (t, 4H, J=7.4 Hz), 2.89–2.93 (m, 8H), 3.88 (s, 6H), 3.94 (s, 12H), 6.90 (s, 2H), 7.15 (s, 4H) m/z (EI): 755 [M$^+$].

PREPARATION EXAMPLE 13

Synthesis of Ethyl 2-Bromothiazole-4-carboxylate

To a sulfuric acid solution (120 mL) of ethyl 2-aminothiazole-4-carboxylate (7.47 g), copper sulfate (10.91 g) and sodium bromide (8.12 g), a solution of sodium nitrite (3.63 g) in ice water was added dropwise over 15 minutes under ice cooling. The resultant mixture was stirred for 30 minutes and for 2 hours at room temperature. Ether was added to the reaction mixture, and the mixture was washed with water. The resultant water layer was neutralized with sodium hydroxide and extracted with ether. The extract was combined with the previously separated ether layer, washed with saturated brine and dried over anhydrous sodium sulfate. After concentrating the combined ether layer under reduced pressure, the resultant residue was purified by column chromatography on silica gel (chloroform), and the resultant crude crystals were recrystallized from hexane to obtain the title compound.

Yield: 8.00 g (78%). $^1$H-NMR (400 MHz, CDCl$_3$) δ: 1.40 (t, 3H, J=7.1 Hz), 4.49 (q, 2H, J=7.1 Hz), 8.16 (s, 1H).

PREPARATION EXAMPLE 14

Synthesis of Ethyl 2-(3,4,5-Trimethoxyphenylethynyl)-thiazole-4-carboxylate 3,4,5-Trimethoxyphenylacetylene (1.34 g), ethyl 2-bromothiazole-4-carboxylate (1.98 g) and copper iodide (53 mg) were dissolved in a mixed solvent of DMF (3 mL) and triethylamine (6 mL), and to the solution dichlorobis-(triphenylphosphine)palladium (II) (99 mg) was added, and the mixture was stirred at 45° C. for 4 hours under an argon atmosphere. The reaction mixture was diluted with ethyl acetate, washed with 2 M hydrochloric acid, water and saturated brine, dried over anhydrous sodium sulfate. After concentrating the reaction mixture under reduced pressure, the residue was purified by column chromatography on silica gel (hexane:ethyl acetate=4:1 to 3:1) to obtain the title compound.

Yield: 2.45 g (theoretical amount). $^1$H-NMR (400 MHz, CDCl$_3$) δ: 1.42 (t, 3H, J=7.1 Hz), 3.88 (s, 6H), 3.89 (s, 3H), 4.44 (q, 2H, J=7.1 Hz), 6.84 (s, 2H), 8.20 (s, 1H).

PREPARATION EXAMPLE 15

Synthesis of 2-(3,4,5-Trimethoxyphenylethynyl)thiazole-4-carboxylic Acid

Ethyl 2-(3,4,5-trimethoxyphenylethynyl)thiazole-4-carboxylate (200 mg) was suspended in methanol (2 mL), to the suspension a 4 M solution (1 mL) of sodium hydroxide was added, and the mixture was stirred at room temperature for 4 hours. Concentrated hydrochloric acid was added dropwise to the reaction mixture at 0° C. to weakly acidify the reaction mixture. Crystals formed were collected by filtration, washed with water and dried to obtain the title compound.

Yield: 133 mg (73%). $^1$H-NMR (400 MHz, CDCl$_3$) δ: 3.88 (s, 6H), 3.89 (s, 3H), 6.84 (s, 2H), 7.26 (s, 1H), 8.29 (s, 1H).

PREPARATION EXAMPLE 16

Synthesis of 4-Hydroxymethyl-2-(3,4,5-trimethoxyphenyl-ethynyl)thiazole 2-(3,4,5-Trimethoxyphenylethynyl)thiazole-4-carboxylic acid (133 mg) was dissolved in THF (8 mL), and to the solution triethylamine (44 mg) was added, and ethyl chloroformate (48 mg) was then added at 0° C. to stir the mixture for 15 minutes. The reaction mixture was filtered, an aqueous solution (2 mL) of sodium borohydride (16 mg) was added to the filtrate, and the resultant mixture was stirred for 30 minutes. Water was added to the reaction mixture, the resultant mixture was extracted with ethyl acetate. The resultant organic layer was washed with saturated brine and dried over anhydrous sodium sulfate. After concentrating the organic layer under reduced pressure, the residue was purified by column chromatography on silica gel (hexane:ethyl acetate=1:1 to 1:2) to obtain the title compound.

Yield: 78 mg (62%). $^1$H-NMR (400 MHz, CDCl$_3$) δ: 2.70 (br, 1H), 3.87 (s, 6H), 3.88 (s, 3H), 4.82 (s, 2H), 6.83 (s, 2H), 7.26 (s, 1H).

PREPARATION EXAMPLE 17

Synthesis of 4-Chloromethyl-2-(3,4,5-trimethoxyphenyl-ethynyl)thiazole

4-Hydroxymethyl-2-(3,4,5-trimethoxyphenylethynyl)-thiazole (569 mg) was treated in the same manner as in Preparation Example 4 to obtain the title compound.

Yield: 128 mg (21%). $^1$H-NMR (400MHz, CDCl$_3$) δ: 3.87 (s, 6H), 3.88 (s, 3H), 4.72 (s, 2H), 6.84 (s, 2H), 7.35 (s, 1H).

EXAMPLE 7

Synthesis of N,N'-bis[[2-(3,4,5-Trimethoxyphenylethynyl)-thiazol-4-yl]methyl] homopiperazine

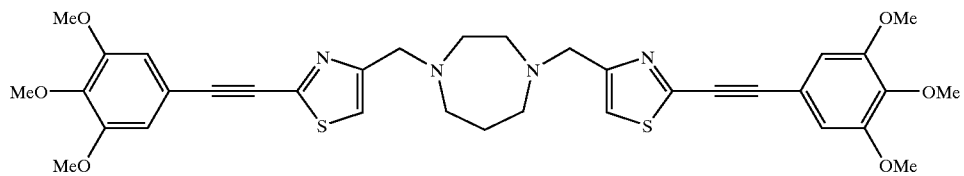

4-Chloromethyl-2-(3,4,5-trimethoxyphenylethynyl)-thiazole (126 mg) and homopiperazine (19 mg) were reacted in the same manner in Example 1 to obtain the title compound as a free base.

Yield: 107 mg (81%). $^1$H-NMR (400 MHz, CDCl$_3$) δ: 1.81–1.89 (m, 2H), 2.81–2.85 (m, 8H), 3.86 (s, 6H), 3.87 (s, 12H), 3.88 (s, 4H), 6.83 (s, 4H), 7.22 (s, 2H).

PREPARATION EXAMPLE 18

Synthesis of Ethyl 2-(3,4,5-Trimethoxybenzamido) thiazole-4-carboxylate 3,4,5-Trimethoxybenzoic acid (3.69 g), ethyl 2-aminothiazole-4-carboxylate (3.0 g) and 4-(dimethylamino)-pyridine (702 mg) were dissolved in dichloromethane (80 mL), and to the solution was added 1-ethyl-3-(3-dimethyl-aminopropyl)carbodiimide hydrochloride (water-soluble carbodiimide hydrochloride) (3.34 g). The mixture was stirred overnight at room temperature and then concentrated under reduced pressure, and the residue was dissolved in ethyl acetate. The solution was successively washed with 2 M hydrochloric acid, a saturated aqueous solution of sodium hydrogencarbonate, water and saturated brine, and dried over anhydrous sodium sulfate. After concentrating the organic layer under reduced pressure, the residue was purified by column chromatography on silica gel (chloroform:methanol=30:1) to obtain the title compound.

Yield: 5.24 g (82%). $^1$H-NMR (400 MHz, CDCl$_3$) δ: 1.22 (t, 3H, J=7.1 Hz), 3.76 (s, 6H), 3.84 (s, 3H), 4.15 (q, 2H, J=7.1 Hz), 7.11 (s, 2H), 7.81 (s, 1H).

PREPARATION EXAMPLE 19

Synthesis of 2-(3,4,5-Trimethoxybenzamido) thiazole-4-carboxylic acid

Ethyl 2-(3,4,5-trimethoxybenzamido)thiazole-4-carboxylate (5.05 g) was treated in the same manner as in Preparation Example 15 to obtain the title compound.

Yield: 4.62 g (99.1%). $^1$H-NMR (400 MHz, CDCl$_3$) δ: 3.73 (s, 3H), 3.86 (s, 6H), 7.50 (s, 2H), 8.03 (s, 1H).

PREPARATION EXAMPLE 20

Synthesis of 4-Hydroxymethyl-2-(3,4,5-trimethoxy-benzamido)thiazole 2-(3,4,5-Trimethoxybenzamido)thiazole-4-carboxylic acid (4.62 g) was treated in the same manner as in Preparation Example 16 to obtain the title compound.

Yield: 1.60 g (36%). $^1$H-NMR (400 MHz, CDCl$_3$) δ: 1.58 (br, 1H), 3.93 (s, 3H), 3.94 (s, 6H), 4.71 (s, 2H), 6.89 (s, 1H), 7.20 (s, 2H).

PREPARATION EXAMPLE 21

Synthesis of 4-Chloromethyl-2-(3,4,5-trimethoxybenzamido)-thiazole

4-Hydroxymethyl-2-(3,4,5-trimethoxybenzamido)-thiazole (900 mg) was treated in the same manner as in Preparation Example 7 to obtain the title compound.

Yield: 593 mg (62%). $^1$H-NMR (400 MHz, CDCl$_3$) δ: 3.92 (s, 6H), 3.93 (s, 3H), 4.56 (s, 2H), 6.98 (s, 1H), 7.24 (s, 2H).

EXAMPLE 8

Synthesis of N,N'-bis[[2-(3,4,5-Trimethoxybenzamido)-thiazol-4-yl]methyl] piperazine

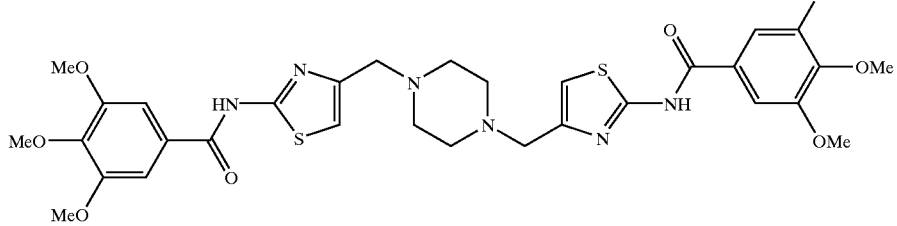

4-Chloromethyl-2-(3,4,5-trimethoxybenzamido)-thiazole (140 mg) and piperazine (17 mg) were reacted in the same manner in Example 1 to obtain the title compound as a free base.

Yield: 38 mg (28%). $^1$H-NMR (400 MHz, CDCl$_3$) δ: 1.98 (br, 8H), 3.15 (s, 4H), 3.75 (s, 12H), 3.90 (s, 6H), 6.71 (s, 2H), 7.16 (s, 4H). m/z (EI): 771 [M$^+$].

EXAMPLE 9

Synthesis of N,N'-bis[[2-(3,4,5-Trimethoxybenzamido)-thiazol-4-yl]methyl] homopiperazine

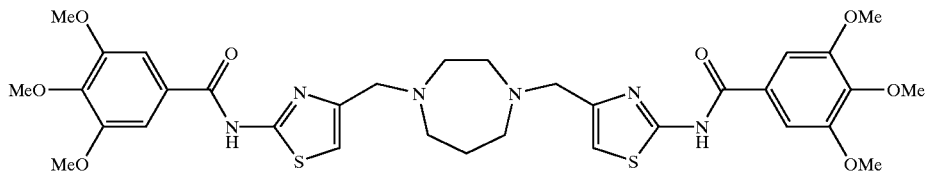

4-Chloromethyl-2-(3,4,5-trimethoxybenzamido)-thiazole (140 mg) and homopiperazine (20 mg) were reacted in the same manner in Example 1 to obtain the title compound as a free base.

Yield: 51 mg (36%). $^1$H-NMR (400 MHz, CDCl$_3$) δ: 1.41 (br, 2H), 2.12–2.35 (m, 8H), 3.73 (s, 12H), 3.89 (s, 6H), 6.69 (s, 2H), 7.18 (s, 4H). m/z (EI): 785 [M$^+$].

PREPARATION EXAMPLE 22

Synthesis of Ethyl 4-Methyl-2-(3,4,5-trimethoxyphenyl)-thiazole-5-carboxylate 3,4,5-Trimethoxyphenylbenzothioamide (3.0 g) and ethyl 2-chloroacetoacetate (2.17 g) were added to ethanol (25 mL), and the mixture was stirred at 80° C. for 7 hours. The reaction mixture was concentrated under reduced pressure, the residue was dissolved in ethyl acetate, and the solution was successively washed with a saturated aqueous solution of sodium hydrogencarbonate, water and saturated brine, dried over anhydrous sodium sulfate and concentrated under reduced pressure. The residue was then recrystallized from hexane-ethyl acetate to obtain the title compound.

Yield: 3.10 g (70%). $^1$H-NMR (400 MHz, CDCl$_3$) δ: 1.39 (t, 3H, J=7.1 Hz), 2.77 (s, 3H), 3.90 (s, 3H), 3.95 (s, 6H), 4.36 (q, 2H, J=7.1 Hz), 7.20 (s, 2H).

PREPARATION EXAMPLE 23

Synthesis of 5-Hydroxymethyl-4-methyl-2-(3,4,5-trimethoxy-phenyl)thiazole

Ethyl 4-methyl-2-(3,4,5-trimethoxyphenyl)thiazole-5-carboxylate (1.0 g) was treated in the same manner as in Preparation Example 3 to obtain the title compound.

Yield: 909 mg (theoretical amount) $^1$H-NMR (400 MHz, CDCl$_3$) δ: 1.62 (br, 1H), 2.45 (s, 3H), 3.89 (s, 3H), 3.94 (s, 6H), 4.82 (s, 2H), 7.13 (s, 2H).

PREPARATION EXAMPLE 24

Synthesis of 5-Chloromethyl-4-methyl-2-(3,4,5-trimethoxy-phenyl)thiazole

5-Hydroxymethyl-4-methyl-2-(3,4,5-trimethoxy-phenyl)thiazole (100 mg) was treated in the same manner as in Preparation Example 4 to obtain the title compound.

Yield: 104 mg (theoretical amount). $^1$H-NMR (400 MHz, CDCl$_3$) δ: 2.79 (s, 3H), 3.96 (s, 3H), 4.03 (s, 6H), 4.73 (s, 2H), 7.62 (s, 2H).

EXAMPLE 10

Synthesis of N,N'-bis[[4-Methyl-2-(3,4,5-trimethoxy-phenyl)thiazol-5-yl]methyl]piperazine

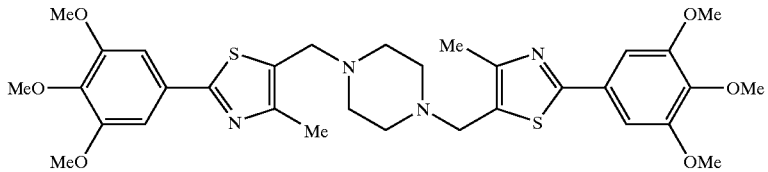

5-Chloromethyl-4-methyl-2-(3,4,5-trimethoxy-phenyl) thiazole (104 mg) and piperazine (13 mg) were reacted in the same manner in Example 1 to obtain the title compound as a free base.

Yield: 60 mg (58%). $^1$H-NMR (400 MHz, CDCl$_3$) δ: 2.41 (s, 6H), 2.58 (br, 8H), 3.66 (s, 4H), 3.88 (s, 6H), 3.93 (s, 12H), 7.13 (s, 4H). m/z (EI): 713 [M$^+$].

EXAMPLE 11

Synthesis of N,N'-bis[[4-Methyl-2-(3,4,5-trimethoxy-phenyl)thiazol-5-yl]methyl] homopiperazine Dimaleate

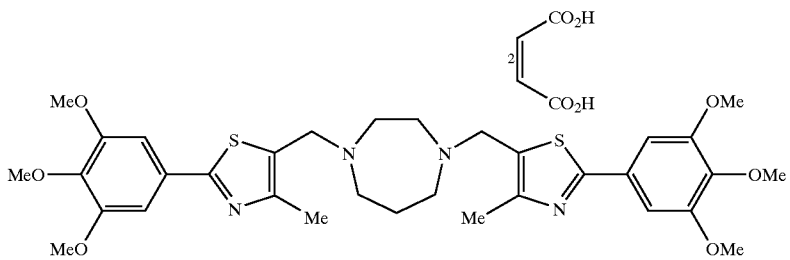

5-Chloromethyl-4-methyl-2-(3,4,5-trimethoxy-phenyl) thiazole (169 mg) and homopiperazine (25 mg) were reacted in the same manner in Example 1 to obtain a product as a free base. The intended product was then dissolved in chloroform-methanol, and to the solution maleic acid was added, and the reaction mixture was concentrated under reduced pressure and then recrystallized from methanol-ether to obtain the title compound as a dimaleate.

Yield: 57 mg (25%). $^1$H-NMR (measured as a free base, 400 MHz, CDCl$_3$) δ: 1.80–1.86 (m, 2H), 2.41 (s, 6H), 2.76–2.81 (m, 8H), 3.78 (s, 4H), 3.88 (s, 6H), 3.93 (s, 12H), 7.13 (s, 4H). m/z (EI): 727 [M$^+$].

PREPARATION EXAMPLE 25

Synthesis of Ethyl 4-Hydroxy-2-oxo-4-(3,4,5-trimethoxy-phenyl)-3-butenoate

3',4',5'-Trimethoxyacetophenone (12.0 g) was dissolved in THF (50 mL), and potassium tert-butoxide (8.16 g) was added to the solution at 0° C. A THF solution (20 mL) of diethyl oxalate (11.4 g) was then added dropwise to the mixture, and the resultant mixture was stirred for 1 hour. A saturated aqueous solution of ammonium chloride was added to the reaction mixture, and the resultant mixture was extracted with ethyl acetate. The resultant organic layer was washed with saturated brine, dried over anhydrous sodium sulfate and concentrated under reduced pressure. The resultant crude crystals were recrystallized from chloroform-hexane to obtain the title compound.

Yield: 13.56 g (78%). $^1$H-NMR (400 MHz, CDCl$_3$) δ: 1.42 (t, 3H, J=7.1 Hz), 1.55 (br, 1H), 3.94 (s, 6H), 3.95 (s, 3H), 4.41 (q, 2H, J=7.1 Hz), 7.02 (s, 1H), 7.24 (s, 2H).

PREPARATION EXAMPLE 26

Synthesis of Ethyl 1-Methyl-5-(3,4,5-trimethoxyphenyl)-pyrazole-3-carboxylate

Ethyl 4-hydroxy-2-oxo-4-(3,4,5-trimethoxyphenyl)-3-butenoate (3.0 g) was dissolved in ethanol (30 mL), and to the solution methylhydrazine (468 mg) was added, and the mixture was stirred at 80° C. for 2 hours. The reaction mixture was concentrated under reduced pressure, and the residue was diluted with ethyl acetate, washed with a saturated aqueous solution of sodium hydrogencarbonate and saturated brine, dried over anhydrous sodium sulfate, and concentrated under reduced pressure. The residue was then purified by column chromatography on silica gel (hexane:ethyl acetate=2:1) to obtain the title compound.

Yield: 817 mg (26%). $^1$H-NMR (400 MHz, CDCl$_3$) δ: 1.41 (t, 3H, J=7.2 Hz), 3.89 (s, 6H), 3.91 (s, 3H), 3.96 (s, 3H), 4.43 (q, 2H, J=7.2 Hz), 6.59 (s, 2H), 6.83 (s, 1H).

PREPARATION EXAMPLE 27

Synthesis of Ethyl 1-Methyl-5-(3,4,5-trimethoxyphenyl)-pyrazole-3-carboxylate

The title compound was isolated from the reaction mixture in Preparation Example 26 by column chromatography on silica gel (hexane:ethyl acetate=2:1).

Yield: 1.73 g (56%). $^1$H-NMR (400 MHz, CDCl$_3$) δ: 1.41 (t, 3H, J=7.2 Hz), 3.87 (s, 3H), 3.93 (s, 6H), 4.22 (s, 3H), 4.38 (q, 2H, J=7.2 Hz), 7.02 (s, 2H), 7.07 (s, 1H).

PREPARATION EXAMPLE 28

Synthesis of 3-Hydroxymethyl-1-methyl-5-(3,4,5-trimethoxy-phenyl)pyrazole

Ethyl 1-methyl-5-(3,4,5-trimethoxyphenyl)pyrazole-3-carboxylate (980 mg) was treated in the same manner as in Preparation Example 3 to obtain the title compound.

Yield: 635 mg (75%). ¹H-NMR (400 MHz, CDCl₃) δ: 3.85 (s, 3H), 3.87 (s, 3H), 3.89 (s, 6H), 4.63 (s, 2H), 6.33 (s, 1H), 6.94 (s, 2H).

PREPARATION EXAMPLE 29

Synthesis of 3-Chloromethyl-1-methyl-5-(3,4,5-trimethoxy-phenyl)pyrazole

3-Hydroxymethyl-1-methyl-5-(3,4,5-trimethoxy-phenyl)pyrazole (635 mg) was treated in the same manner as in Preparation Example 4 to obtain the title compound.

Yield: 624 mg (93%). ¹H-NMR (400 MHz, CDCl₃) δ: 3.86 (s, 3H), 3.88 (s, 6H), 3.90 (s, 3H), 4.62 (s, 2H), 6.34 (s, 1H), 6.59 (s, 2H).

EXAMPLE 12

Synthesis of N,N'-bis[[1-Methyl-5-(3,4,5-trimethoxy-phenyl)pyrazol-3-yl]methyl]piperazine

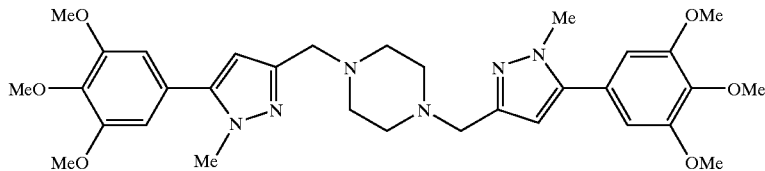

3-Chloromethyl-1-methyl-5-(3,4,5-trimethoxy-phenyl)pyrazole (119 mg) and piperazine (17 mg) were reacted in the same manner in Example 1 to obtain the title compound as a free base.

Yield: 16 mg (13%). ¹H-NMR (400 MHz, CDCl₃) δ: 2.64 (br, 8H), 3.84 (s, 4H), 3.88 (s, 18H), 3.89 (s, 6H), 6.23 (s, 2H), 6.58 (s, 4H). m/z (EI): 606 [M⁺].

EXAMPLE 13

Synthesis of N,N'-bis[[1-Methyl-5-(3,4,5-trimethoxy-phenyl)pyrazol-3-yl]methyl]homopiperazine

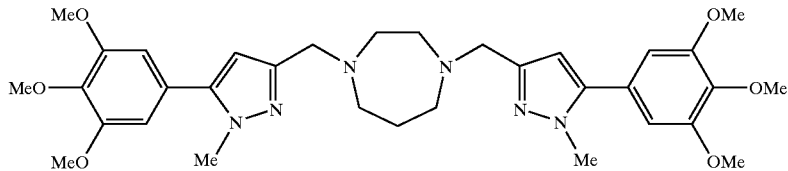

3-Chloromethyl-1-methyl-5-(3,4,5-trimethoxy-phenyl)pyrazole (119 mg) and homopiperazine (20 mg) were reacted in the same manner in Example 1 to obtain the title compound as a free base.

Yield: 73 mg (59%). ¹H-NMR (400 MHz, CDCl₃) δ: 1.92–1.98 (m, 2H), 2.90–2.95 (m, 8H), 3.76 (s, 4H), 3.85 (s, 6H), 3.89 (s, 12H), 3.90 (s, 6H), 6.31 (s, 2H), 6.60 (s, 4H). m/z (EI): 620 [M⁺].

PREPARATION EXAMPLE 30

Synthesis of 5-Hydroxymethyl-1-methyl-3-(3,4,5-trimethoxy-phenyl)pyrazole

Ethyl 1-methyl-3-(3,4,5-trimethoxyphenyl)pyrazole-5-carboxylate (1.97 g) was treated in the same manner as in Preparation Example 3 to obtain the title compound.

Yield: 1.73 g (theoretical amount). ¹H-NMR (400 MHz, CDCl₃) δ: 3.77 (s, 3H), 3.80 (s, 6H), 3.82 (s, 3H), 4.62 (s, 2H), 6.29 (s, 1H), 6.51 (s, 2H).

PREPARATION EXAMPLE 31

Synthesis of 5-Chloromethyl-1-methyl-3-(3,4,5-trimethoxy-phenyl)pyrazole

5-Hydroxymethyl-1-methyl-3-(3,4,5-trimethoxy-phenyl)pyrazole (1.73 g) was treated in the same manner as in Preparation Example 4 to obtain the title compound.

Yield: 1.70 g (92%). ¹H-NMR (400 MHz, CDCl₃) δ: 3.83 (s, 3H), 3.88 (s, 6H), 3.91 (s, 3H), 4.58 (s, 2H), 6.49 (s, 1H), 6.95 (s, 2H).

EXAMPLE 14

Synthesis of N,N'-bis[[1-Methyl-3-(3,4,5-trimethoxy-phenyl)pyrazol-5-yl]methyl]piperazine

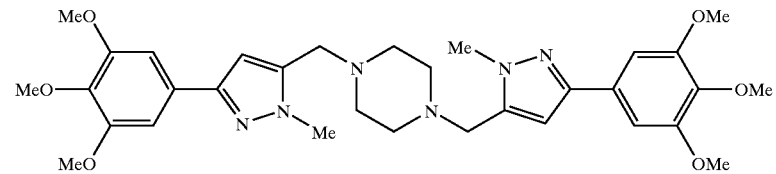

5-Chloromethyl-1-methyl-3-(3,4,5-trimethoxy-phenyl)pyrazole (119 mg) and piperazine (17 mg) were reacted in the same manner in Example 1 to obtain the title compound as a free base.

Yield: 56 mg (46%). $^1$H-NMR (400 MHz, CDCl$_3$) δ: 2.48 (br, 8H), 3.52 (s, 4H), 3.86 (s, 6H), 3.92 (s, 18H), 6.39 (s, 2H), 6.99 (s, 4H). m/z (EI): 606 [M$^+$].

EXAMPLE 15

Synthesis of N,N'-bis[[1-Methyl-3-(3,4,5-trimethoxy-phenyl)pyrazol-5-yl]methyl]homopiperazine

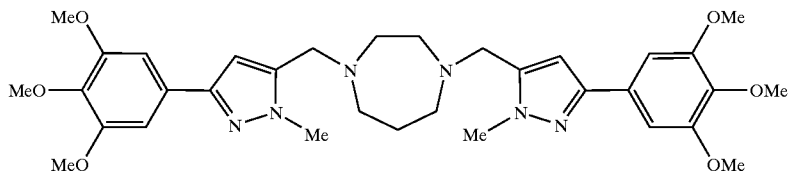

5-Chloromethyl-1-methyl-3-(3,4,5-trimethoxy-phenyl)pyrazole (119 mg) and homopiperazine (20 mg) were reacted in the same manner in Example 1 to obtain the title compound as a free base.

Yield: 135 mg (theoretical amount) $^1$H-NMR (400 MHz, CDCl$_3$) δ: 1.70–1.78 (m, 2H), 2.57–2.66 (m, 8H), 3.54 (s, 4H), 3.79 (s, 6H), 3.85 (s, 12H), 3.87 (s, 6H), 6.30 (s, 2H), 6.94 (s, 4H). m/z (EI):620 [M$^+$].

PREPARATION EXAMPLE 32

Synthesis of Ethyl 1-Benzyl-5-(3,4,5-trimethoxyphenyl)-pyrazole-3-carboxylate

Ethyl 4-hydroxy-2-oxo-4-(3,4,5-trimethoxyphenyl)-3-butenoate (3.12 g) and benzylhydrazine hydrochloride (1.59 g) were treated in the same manner as in Preparation Example 26 to obtain the title compound.

Yield: 3.71 g (93%). $^1$H-NMR (400 MHz, CDCl$_3$) δ: 1.33 (t, 3H, J=7.1 Hz), 3.55 (s, 6H), 3.76 (s, 3H), 4.35 (q, 2H, J=7.1 Hz), 5.36 (s, 2H), 6.33 (s, 2H), 6.80 (s, 1H), 6.97 (d, 2H, J=6.8 Hz), 7.13–7.23 (m, 3H).

PREPARATION EXAMPLE 33

Synthesis of 1-Benzyl-3-hydroxymethyl-5-(3,4,5-trimethoxy-phenyl)pyrazole

Ethyl 1-benzyl-5-(3,4,5-trimethoxyphenyl)-pyrazole-3-carboxylate (3.35 g) was treated in the same manner as in Preparation Example 3 to obtain the title compound.

Yield: 3.29 g (theoretical amount). $^1$H-NMR (400 MHz, CDCl$_3$) δ: 3.65 (s, 6H), 3.85 (s, 3H), 4.73 (s, 2H), 5.32 (s, 2H), 6.35 (s, 1H), 6.44 (s, 2H), 7.07 (d, 2H, J=6.8 Hz), 7.21–7.31 (m, 3H).

PREPARATION EXAMPLE 33

Synthesis of 1-Benzyl-3-chloromethyl-5-(3,4,5-trimethoxy-phenyl)pyrazole

1-Benzyl-3-hydroxymethyl-5-(3,4,5-trimethoxy-phenyl)pyrazole (2.93 g) was treated in the same manner as in Preparation Example 4 to obtain the title compound.

Yield: 2.57 g (83%). $^1$H-NMR (400 MHz, CDCl$_3$) δ: 3.65 (s, 6H), 3.86 (s, 3H), 4.67 (s, 2H), 5.32 (s, 2H), 6.41 (s, 1H), 6.44 (s, 2H), 7.07 (d, 2H, J=6.8 Hz), 7.22–7.33 (m, 3H).

EXAMPLE 16

Synthesis of N,N'-bis[[1-Benzyl-5-(3,4,5-trimethoxy-phenyl)pyrazol-3-yl]methyl]piperazine

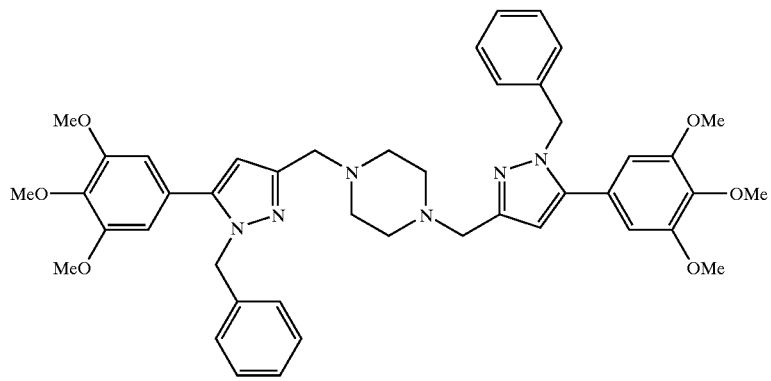

1-Benzyl-3-chloromethyl-5-(3,4,5-trimethoxy-phenyl)pyrazole (559 mg) and piperazine (59 mg) were reacted in the same manner in Example 1 to obtain the title compound as a free base.

Yield: 186 mg (36%). $^1$H-NMR (400 MHz, CDCl$_3$) δ: 2.69 (s, 8H), 3.65 (s, 12H), 3.68 (s, 4H), 3.85 (s, 6H), 5.33 (s, 4H), 6.33 (s, 2H), 6.44 (s, 4H), 7.02–7.06 (m, 4H), 7.20–7.30 (m, 6H). m/z (EI): 758 [M$^+$].

EXAMPLE 17

Synthesis of N,N'-bis[[1-Benzyl-5-(3,4,5-trimethoxy-phenyl)pyrazol-3-yl]methyl]homopiperazine

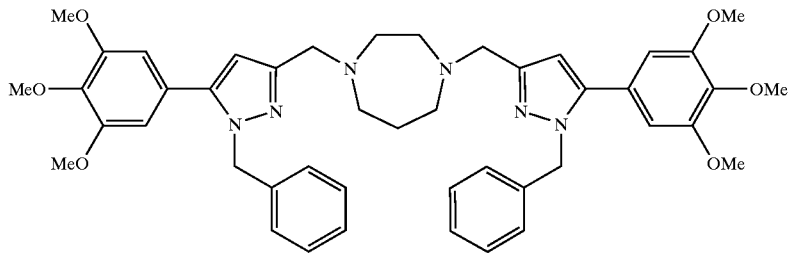

1-Benzyl-3-chloromethyl-5-(3,4,5-trimethoxy-phenyl)pyrazole (559 mg) and homopiperazine (68 mg) were reacted in the same manner in Example 1 to obtain the title compound as a free base.

Yield: 222 mg (42%). $^1$H-NMR (400 MHz, CDCl$_3$) δ: 1.95–2.25 (m, 2H), 2.96–2.98 (m, 8H), 3.65 (s, 12H), 3.85 (s, 10H), 5.34 (s, 4H), 6.42 (s, 2H), 6.45 (s, 4H), 7.05 (d, 4H, J=7.1 Hz), 7.20–7.31 (m, 6H). m/z (EI): 772 [M$^+$].

PREPARATION EXAMPLE 35

Synthesis of Ethyl 5-(3,4,5-Trimethoxyphenyl)pyrazole-3-carboxylate

Ethyl 4-hydroxy-2-oxo-3,4,5-trimethoxyphenyl-3-butenoate (5.0 g) and hydrazine monohydrate (0.8 mL) were treated in the same manner as in Preparation Example 26 to obtain the title compound.

Yield: 3.32 g (67%). $^1$H-NMR (400 MHz, CDCl$_3$) δ: 1.22 (t, 3H, J=7.1 Hz), 3.83 (s, 6H), 3.86 (s, 3H), 4.20 (q, 2H, J=7.1 Hz), 6.93 (s, 1H), 6.97 (s, 2H).

PREPARATION EXAMPLE 36

Synthesis of Ethyl 1-Methoxymethyl-5-(3,4,5-trimethoxy-phenyl)pyrazole-3-carboxylate Ethyl 5-(3,4,5-trimethoxyphenyl)pyrazole-3-carboxylate (1.70 g) was dissolved in dichloromethane (50 mL), and to the solution diisopropylethylamine (933 mg) was added at 0° C., and chloromethyl methyl ether (581 mg) was then added thereto. The resultant mixture was stirred at room temperature for 30 minutes under an argon atmosphere. The reaction mixture was washed with water and saturated brine, dried over anhydrous sodium sulfate and then concentrated under reduced pressure to obtain the title compound.

Yield: 820 mg (42%). $^1$H-NMR (400 MHz, CDCl$_3$) δ: 1.42 (t, 3H, J=7.2 Hz), 3.40 (s, 3H), 3.88 (s, 3H), 3.94 (s, 6H), 4.40 (q, 2H, J=7.2 Hz), 5.85 (s, 2H), 7.06 (s, 2H), 7.17 (s, 1H).

PREPARATION EXAMPLE 37

Synthesis of 3-Hydroxymethyl-1-methoxymethyl-5-(3,4,5-trimethoxyphenyl)pyrazole

Ethyl 1-methoxymethyl-5-(3,4,5-trimethoxyphenyl)-pyrazole-3-carboxylate (820 mg) was treated in the same manner as in Preparation Example 3 to obtain the title compound.

Yield: 449 mg (62%). $^1$H-NMR (400 MHz, CDCl$_3$) δ: 2.74 (br, 1H), 3.37 (s, 3H), 3.86 (s, 3H), 3.92 (s, 6H), 4.74 (d, 2H, J=5.9 Hz), 5.51 (s, 2H), 6.55 (s, 1H), 7.01 (s, 2H).

PREPARATION EXAMPLE 38

Synthesis of 3-Chloromethyl-1-methoxymethyl-5-(3,4,5-trimethoxyphenyl)pyrazole

3-Hydroxymethyl-1-methoxymethyl-5-(3,4,5-trimethoxyphenyl)pyrazole (449 mg) was treated in the same manner as in Preparation Example 4 to obtain the title compound.

Yield: 152 mg (32%). $^1$H-NMR (400 MHz, CDCl$_3$) δ: 3.34 (s, 3H), 3.84 (s, 3H), 3.90 (s, 6H), 4.69 (s, 2H), 5.52 (s, 2H), 6.61 (s, 1H), 6.98 (s, 2H).

PREPARATION EXAMPLE 39

Synthesis of N,N'-bis[[1-Methoxymethyl-5-(3,4,5-trimethoxyphenyl)pyrazol-3-yl]methyl]piperazine 3-Chloromethyl-1-methoxymethyl-5-(3,4,5-trimethoxyphenyl)pyrazole (101 mg) and piperazine (13 mg) were reacted in the same manner in Example 1 to obtain the title compound.

Yield: 71 mg (69%). $^1$H-NMR (400 MHz, CDCl$_3$) δ: 2.50 (br, 8H), 3.35 (s, 6H), 3.62 (s, 4H), 3.86 (s, 6H), 3.93 (s, 12H), 5.57 (s, 4H), 6.48 (s, 2H), 7.02 (s, 4H).

EXAMPLE 18

Synthesis of N,N'-bis[[5-(3,4,5-Trimethoxyphenyl)pyrazol-3-yl]methyl]piperazine Dihydrochloride

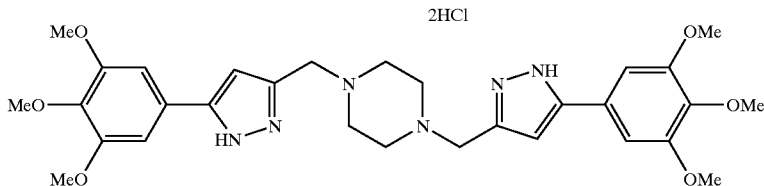

N,N'-Bis[[1-methoxymethyl-5-(3,4,5-trimethoxy-phenyl)pyrazol-3-yl]methyl]piperazine (71 mg) was dissolved in chloroform (3 mL), and to the solution an ethyl acetate solution (0.7 mL) of 4 M hydrochloric acid was added at room temperature, and the mixture was stirred for 3 hours. After concentrating the reaction mixture, the residue was sufficiently dried and recrystallized from methanol-diisopropyl ether to obtain the title compound.

Yield: 54 mg (79%). $^1$H-NMR (400 MHz, DMSO-$d_6$) δ: 3.15 (br, 8H), 3.69 (s, 6H), 3.83 (s, 12H), 4.20 (s, 4H), 6.81 (s, 2H), 7.05 (s, 4H).

PREPARATION EXAMPLE 40

Synthesis of N,N'-bis[[1-Methoxymethyl-5-(3,4,5-trimethoxyphenyl)pyrazol-3-yl]methyl]homopiperazine 3-Chloromethyl-1-methoxymethyl-5-(3,4,5-trimethoxyphenyl)pyrazole (95 mg) and homopiperazine (14 mg) were reacted in the same manner in Example 1 to obtain the title compound.

Yield: 75 mg (77%). $^1$H-NMR (400 MHz, CDCl$_3$) δ: 1.79–1.81 (m, 2H), 2.67–2.75 (m, 8H), 3.36 (s, 6H), 3.86 (s, 4H), 3.86 (s, 6H), 3.92 (s, 12H), 5.60 (s, 4H), 6.45 (s, 2H), 7.02 (s, 4H).

EXAMPLE 19

Synthesis of N,N'-bis[[5-(3,4,5-Trimethoxyphenyl)pyrazol-3-yl]methyl]homopiperazine Dihydrochloride

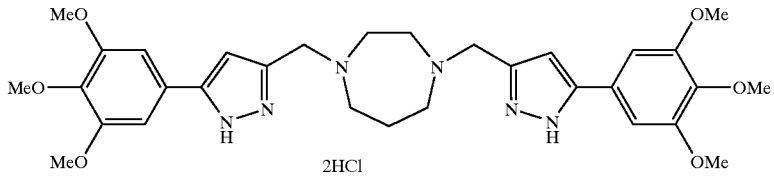

N,N'-Bis[[1-methoxymethyl-5-(3,4,5-trimethoxy-phenyl)pyrazol-3-yl]methyl]homopiperazine (75 mg) was treated in the same manner as in Example 18 to obtain the title compound.

Yield: 60 mg (73%). $^1$H-NMR (400 MHz, CDCl$_3$) δ: 2.19 (br, 2H), 3.42 (br, 4H), 3.69 (s, 6H), 3.81 (br, 4H), 3.83 (s, 12H), 4.31 (s, 4H), 6.89 (s, 2H), 7.06 (s, 4H).

PREPARATION EXAMPLE 41

Synthesis of Ethyl 1-(3-Pyridylmethyl)-5-(3,4,5-trimethoxyphenyl)pyrazole-3-carboxylate Ethyl 1-methoxymethyl-5-(3,4,5-trimethoxyphenyl)-pyrazole-3-carboxylate (820 mg) was dissolved in DMF (4 mL), and to the solution potassium carbonate (325 mg) and 3-picolyl chloride hydrochloride (193 mg) were added, and the mixture was stirred at 50° C. for 3 hours. The reaction mixture was concentrated under reduced pressure, and the residue was diluted with ethyl acetate, washed with water and saturated brine and dried over anhydrous sodium sulfate. After concentrating the diluted residue, the resultant residue was purified by column chromatography on silica gel (hexane:ethyl acetate=1:2 to 0:1) to obtain the title compound.

Yield: 354 mg (91%). $^1$H-NMR (400 MHz, CDCl$_3$) δ: 1.27 (t, 3H, J=7.1 Hz), 3.79 (s, 3H), 3.84 (s, 6H), 4.24 (q, 2H, J=7.1 Hz), 5.72 (s, 2H), 6.98 (s, 2H), 7.06 (s, 1H), 7.13 (dd, 1H, J=7.8 Hz, 4.8 Hz), 7.53 (d, 1H, J=7.9 Hz), 8.42 (d, 1H, J=3.4 Hz), 8.54 (s, 1H).

PREPARATION EXAMPLE 42

Synthesis of 3-Hydroxymethyl-1-(3-pyridylmethyl)-5-(3,4,5-trimethoxyphenyl)pyrazole Ethyl 1-(3-pyridylmethyl)-5-(3,4,5-trimethoxy-phenyl)pyrazole-3-carboxylate (344 mg) was treated in the same manner as in Preparation Example 3 to obtain the title compound.

Yield: 295 mg (96%). $^1$H-NMR (400 MHz, CDCl$_3$) δ: 1.64 (br, 1H), 3.87 (s, 3H), 3.91 (s, 6H), 4.63 (s, 2H), 5.45 (s, 2H), 6.48 (s, 1H), 7.00 (s, 2H), 7.24 (dd, 1H, J=7.9 Hz, 4.9 Hz), 7.56 (d, 1H, J=7.8 Hz), 8.49 (br, 2H).

PREPARATION EXAMPLE 43

Synthesis of 3-Chloromethyl-1-(3-pyridylmethyl)-5-(3,4,5-trimethoxyphenyl)pyrazole 3-Hydroxymethyl-1-(3-pyridylmethyl)-5-(3,4,5-trimethoxyphenyl)pyrazole (290 mg) was treated in the same manner as in Preparation Example 4 to obtain the title compound.

Yield: 230 mg (75%). $^1$H-NMR (400 MHz, CDCl$_3$) δ: 3.87 (s, 3H), 3.92 (s, 6H), 4.52 (s, 2H), 5.49 (s, 2H), 6.60 (s, 1H), 7.01 (s, 2H), 7.27 (dd, 1H, J=8.2 Hz, 4.4 Hz), 7.54 (d, 1H, J=7.9 Hz), 8.56 (d, 1H, J=2.9 Hz), 8.57 (s, 1H).

EXAMPLE 20

Synthesis of N,N'-bis[[1-(3-Pyridylmethyl)-5-(3,4,5-trimethoxyphenyl)pyrazol-3-yl]methyl]piperazine

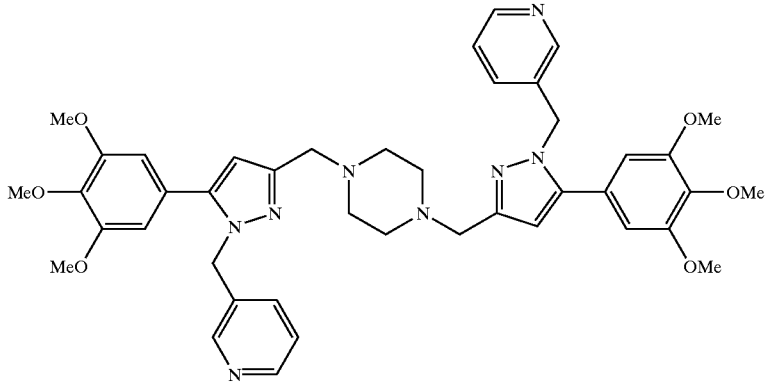

3-Chloromethyl-1-(3-pyridylmethyl)-5-(3,4,5-trimethoxyphenyl)pyrazole (110 mg) and piperazine (12 mg) were reacted in the same manner in Example 1 to obtain the title compound as a free base.

Yield: 47 mg (44%). $^1$H-NMR (400 MHz, CDCl$_3$) δ: 2.28 (br, 8H), 3.36 (s, 4H), 3.87 (s, 6H), 3.93 (s, 12H), 5.48 (s, 4H), 6.43 (s, 2H), 7.02 (s, 4H), 7.23 (dd, 2H, J=7.8 Hz, 4.8 Hz), 7.50 (d, 2H, J=7.9 Hz), 8.51 (br, 4H). m/z (EI): 760 [M$^+$].

EXAMPLE 21

Synthesis of N,N'-bis[[1-(3-Pyridylmethyl)-5-(3,4,5-trimethoxyphenyl)pyrazol-3-yl]methyl]homopiperazine

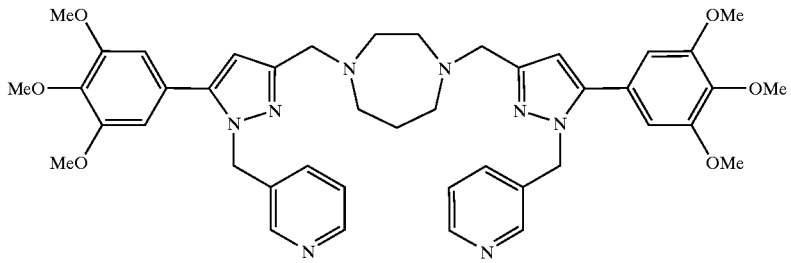

3-Chloromethyl-1-(3-pyridylmethyl)-5-(3,4,5-trimethoxyphenyl)pyrazole (110 mg) and homopiperazine (13 mg) were reacted in the same manner in Example 1 to obtain the title compound as a free base.

Yield: 58 mg (56%). $^1$H-NMR (400 MHz, CDCl$_3$) δ: 1.67–1.72 (m, 2H), 2.49–2.60 (m, 8H), 3.47 (s, 4H), 3.86 (s, 6H), 3.92 (s, 12H), 5.53 (s, 4H), 6.41 (s, 2H), 7.02 (s, 4H), 7.24 (dd, 2H, J=7.9 Hz, 4.9 Hz), 7.50 (d, 2H, J=7.9 Hz), 8.51–8.52 (m, 4H). m/z (EI): 774[M$^+$].

PREPARATION EXAMPLE 44

Synthesis of Ethyl 5-(3,4,5-Trimethoxyphenyl)isoxazole-3-carboxylate

3',4',5'-Trimethoxyacetophenone (98%, 10.89 g) was suspended at −78° C. under an argon atmosphere, and a hexane solution (31.9 mL) of 1.59 M n-butyllithium was slowly added dropwise to the suspension. After 10 minutes, the suspension became homogeneous. Diethyl oxalate (8.16 g) was added dropwise to the homogeneous suspension, and the resultant mixture was stirred at the same temperature for 1 hour. A saturated aqueous solution (5 mL) of ammonium chloride was added to the reaction mixture and warmed to room temperature to conduct extraction with ethyl acetate. The resultant organic layer was washed with saturated brine, dried over anhydrous sodium sulfate and concentrated under reduced pressure to obtain a yellow oil. The yellow oil was dissolved in ethanol (100 mL), and to the solution an aqueous solution (10 mL) of hydroxylamine hydrochloride (3.52 g), and the resultant mixture was refluxed for 1 hour. After the reaction mixture was concentrated under reduced pressure, the residue was diluted with ethyl acetate, washed with water and saturated brine and dried over anhydrous sodium sulfate. After the diluted residue was concentrated under reduced pressure, the residue was purified by column chromatography on silica gel (hexane:ethyl acetate=3:1) to obtain the title compound.

Yield: 7.25 g (46%). $^1$H-NMR (400 MHz, CDCl$_3$) δ: 1.45 (t, 3H, J=7.1 Hz), 3.90 (s, 3H), 3.94 (s, 6H), 4.48 (q, 2H, J=7.1 Hz), 6.86 (s, 1H), 7.02 (s, 2H).

PREPARATION EXAMPLE 45

Synthesis of 3-Hydroxymethyl-5-(3,4,5-trimethoxyphenyl)-isoxazole

Ethyl 5-(3,4,5-trimethoxyphenyl)isoxazole-3-carboxylate (3.0 g) was treated in the same manner as in Preparation Example 3 to obtain the title compound.

Yield: 1.72 g (67%). $^1$H-NMR (400 MHz, CDCl$_3$) δ: 1.56 (s, 1H), 3.90 (s, 3H), 3.93 (s, 6H), 4.81 (s, 2H), 6.53 (s, 1H), 7.00 (s, 2H).

PREPARATION EXAMPLE 46

Synthesis of 3-Chloromethyl-5-(3,4,5-trimethoxyphenyl)-isoxazole

3-Hydroxymethyl-5-(3,4,5-trimethoxyphenyl)isoxazole (1.62 g) was dissolved in pyridine (10 mL), and lithium chloride (336 mg) was added to the solution. Methanesulfonyl chloride (908 mg) was added dropwise to the resultant mixture under ice cooling, and the mixture was stirred at room temperature for 2 hours. The reaction mixture was diluted with ethyl acetate, washed with 2 M hydrochloric acid, water and saturated brine, dried over anhydrous sodium sulfate and concentrated under reduced pressure. The residue was then purified by column chromatography on silica gel (hexane:ethyl acetate=3:1) to obtain the title compound.

Yield: 766 mg (44%). $^1$H-NMR (400 MHz, CDCl$_3$) δ: 3.90 (s, 3H), 3.93 (s, 6H), 4.63 (s, 2H), 6.58 (s, 1H), 6.99 (s, 2H).

EXAMPLE 22

Synthesis of N,N'-bis[[5-(3,4,5-Trimethoxyphenyl)isoxazol-3-yl]methyl]piperazine

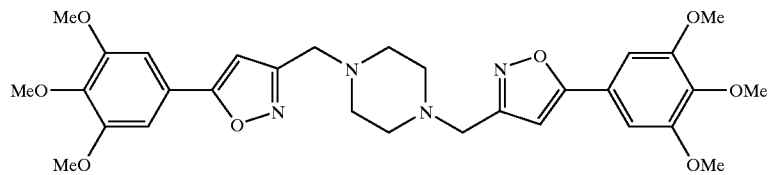

3-Chloromethyl-5-(3,4,5-trimethoxyphenyl)isoxazole (170 mg) and piperazine (26 mg) were reacted in the same manner in Example 1 to obtain the title compound as a free base.

Yield: 129 mg (74%). $^1$H-NMR (400 MHz, CDCl$_3$) δ: 2.60 (br, 8H), 3.65 (s, 4H), 3.89 (s, 6H), 3.92 (s, 12H), 6.50 (s, 2H), 7.04 (s, 4H). m/z (EI): 580 [M$^+$].

EXAMPLE 23

Synthesis of N,N'-bis[(5-(3,4,5-Trimethoxyphenyl)isoxazol-3-yl)methyl]homopiperazine

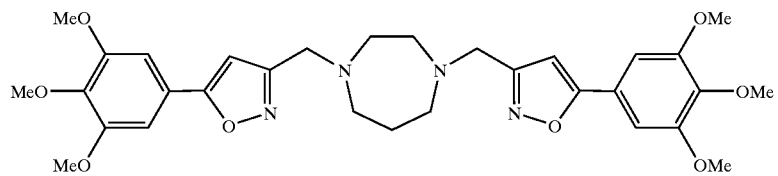

3-Chloromethyl-5-(3,4,5-trimethoxyphenyl)isoxazole (170 mg) and homopiperazine (30 mg) were reacted in the same manner in Example 1 to obtain the title compound as a free base.

Yield: 182 mg (theoretical amount). $^1$H-NMR (400 MHz, CDCl$_3$) δ: 1.83–1.86 (m, 2H), 2.79–2.84 (m, 8H), 3.78 (s, 4H), 3.89 (s, 6H), 3.92 (s, 12H), 6.51 (s, 2H), 6.99 (s, 4H). m/z (EI): 594 [M$^+$].

PREPARATION EXAMPLE 47

Synthesis of O-tert-Butyldimethylsilyl-L-serine methyl ester

L-Serine methyl ester hydrochloride (7.09 g) was suspended in dichloromethane (100 mL), and to the suspension 4-(dimethylamino)pyridine (700 mg) and triethylamine (9.69 g) were added, and tert-butyldimethylchlorosilane (7.0 g) were added portionwise at 0° C. to the mixture to conduct stirring at room temperature. The reaction mixture was washed with water and saturated brine, dried over anhydrous sodium sulfate and concentrated under reduced pressure. The residue was purified by column chromatography on silica gel (chloroform:methanol=20:1) to obtain the title compound.

Yield: 10.15 g (96%). $^1$H-NMR (400 MHz, CDCl$_3$) δ: 0.05 (s, 6H), 0.87 (s, 9H), 1.75 (br, 2H), 3.52 (t, 1H, J=4.0 Hz), 3.73 (s, 3H), 3.81 (dd, 1H, J=9.8 Hz, 3.8 Hz), 3.92 (dd, 1H, J=9.5 Hz, 4.4 Hz).

PREPARATION EXAMPLE 48

Synthesis of O-tert-Butyldimethylsilyl-N-(3,4,5-trimethoxybenzoyl)-L-serine Methyl Ester 3,4,5-Trimethoxybenzoic acid (8.36 g) was dissolved in dichloromethane (150 mL), and to the solution

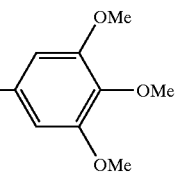

4-(dimethylamino)pyridine (800 mg) and O-tert-butyldimethyl-silyl-L-serine methyl ester (10.15 g) were added. To the resultant mixture, water-soluble carbodiimide hydrochloride (7.77 g) was added portionwise at 0° C., and the mixture was stirred for 3 hours. The reaction mixture was washed with water and saturated brine, dried over anhydrous sodium sulfate and concentrated under reduced pressure. The residue was then purified by column chromatography on silica gel (chloroform:methanol=100:1 to 50:1) to obtain the title compound.

Yield: 15.91 g (95%).

PREPARATION EXAMPLE 49

Synthesis of N-(3,4,5-Trimethoxybenzoyl)-L-serine Methyl Ester

O-tert-Butyldimethylsilyl-N-(3,4,5-trimethoxy-benzoyl)-L-serine methyl ester (15.91 g) was dissolved in THF (70 mL), and to the solution a THF solution (55.82 mL) of 1.0 M tetrabutylammonium fluoride was added at 0° C., and the mixture was stirred at room temperature for 2 hours. The reaction mixture was concentrated under reduced pressure, and the residue was diluted with ethyl acetate, washed with water and saturated brine, dried over anhydrous sodium sulfate and concentrated under reduced pressure. The resultant crude crystals were then recrystallized from methanol-ether-hexane to obtain the title compound.

Yield: 4.15 g (36%). $^1$H-NMR (400 MHz, CDCl$_3$) δ: 2.67 (br, 1H), 3.83 (s, 3H), 3.89 (s, 3H), 3.91 (s, 6H), 4.06–4.08 (m, 1H), 4.84–4.88 (m, 2H), 7.05 (s, 2H), 7.26 (s, 1H).

PREPARATION EXAMPLE 50

Synthesis of Methyl 2-(3,4,5-Trimethoxyphenyl)-4,5-dihydroxazole-4-carboxylate (Methoxycarbonylsulfamoyl)triethylammonium hydroxide (2.04 g) was dissolved in THF (5 mL) under an argon atmosphere, to the solution a THF suspension (55 mL) of N-(3,4,5-trimethoxybenzoyl)-L-serine methyl ester (2.24 g) was added dropwise at 70° C., and the mixture was stirred for 2 hours. The reaction mixture was concentrated under reduced pressure, and the residue was diluted with ethyl acetate, washed with water and saturated brine, dried over anhydrous sodium sulfate and concentrated under reduced pressure. The residue was then purified by column chromatography on silica gel (hexane:ethyl acetate=1:1) to obtain the title compound.

Yield: 1.38 g (65%). $^1$H-NMR (400 MHz, CDCl$_3$) δ: 3.88 (s, 3H), 3.89 (s, 3H), 3.90 (s, 6H), 4.60 (t, 1H, J=9.6 Hz), 4.70 (t, 1H, J=8.2 Hz), 4.96 (dd, 1H, J=10.4 Hz, 8.1 Hz), 7.24 (s, 2H).

PREPARATION EXAMPLE 51

Synthesis of Methyl 2-(3,4,5-Trimethoxyphenyl)oxazole-4-carboxylate

Methyl 2-(3,4,5-trimethoxyphenyl)-4,5-dihydroxazole-4-carboxylate (1.38 g) was dissolved in dichloromethane (10 mL), and to the solution 1,8-diazabicyclo[5.4.0]-7-undecene (783 mg) was added at 0° C. A solution of bromotrichloromethane (1.02 g) in dichloromethane (20 mL) was then added dropwise to the mixture to stir the resultant mixture for 5 hours. The reaction mixture was diluted with chloroform, washed with a saturated aqueous solution of ammonium chloride and saturated brine, dried over anhydrous sodium sulfate and concentrated under reduced pressure. The residue was then purified by column chromatography on silica gel (chloroform:methanol=50:1) to obtain the title compound.

Yield: 879 mg (64%). $^1$H-NMR (400 MHz, CDCl$_3$) δ: 3.91 (s, 3H), 3.94 (s, 6H), 3.96 (s, 3H), 7.35 (s, 2H), 8.27 (s, 1H).

PREPARATION EXAMPLE 52

Synthesis of 4-Hydroxymethyl-2-(3,4,5-trimethoxyphenyl)-oxazole

Methyl 2-(3,4,5-trimethoxyphenyl)oxazole-4-carboxylate (879 mg) was treated in the same manner as in Preparation Example 3 to obtain the title compound.

Yield: 153 mg (19%).

PREPARATION EXAMPLE 53

Synthesis of 4-Chloromethyl-2-(3,4,5-trimethoxyphenyl)-oxazole

4-Hydroxymethyl-2-(3,4,5-trimethoxyphenyl)oxazole (153 mg) was treated in the same manner as in Preparation Example 46 to obtain the title compound.

Yield: 124 mg (76%). $^1$H-NMR (400 MHz, CDCl$_3$) δ: 3.90 (s, 3H), 3.94 (s, 6H), 4.58 (s, 2H), 7.27 (s, 2H), 7.69 (s, 1H).

EXAMPLE 24

Synthesis of N,N'-bis[[2-(3,4,5-Trimethoxyphenyl)oxazol-4-yl]methyl]piperazine

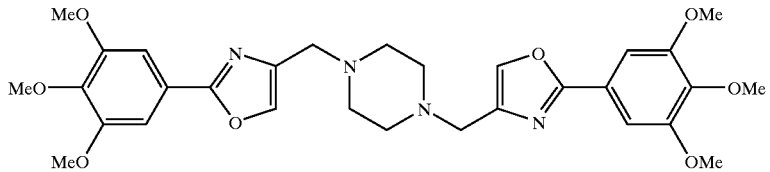

4-Chloromethyl-2-(3,4,5-trimethoxyphenyl)oxazole (124 mg) and piperazine (17 mg) were treated in the same manner in Example 1 to obtain the title compound as a free base.

Yield: 46 mg (40%). $^1$H-NMR (400 MHz, CDCl$_3$) δ: 2.64 (br, 8H), 3.89 (s, 6H), 3.93 (s, 12H), 5.30 (s, 4H), 7.28 (s, 4H), 7.57 (s, 2H). m/z (EI): 580 [M$^+$].

EXAMPLE 25

Synthesis of N,N'-bis[[2-(3,4,5-Trimethoxyphenyl)oxazol-4-yl]methyl]homopiperazine

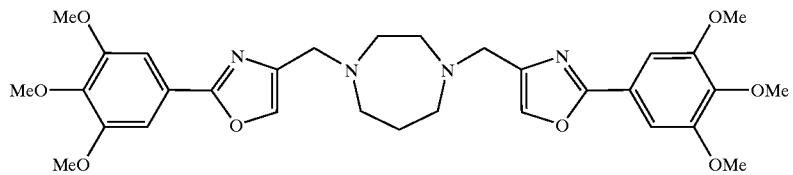

4-Chloromethyl-2-(3,4,5-trimethoxyphenyl)oxazole (111 mg) and homopiperazine (18 mg) were treated in the same manner in Example 1 to obtain the title compound as a free base.

Yield: 60 mg (56%). $^1$H-NMR (400 MHz, CDCl$_3$) δ: 1.83–1.89 (m, 2H), 2.80–2.85 (m, 8H), 3.68 (s, 4H), 3.89 (s, 6H), 3.93 (s, 12H), 7.28 (s, 4H), 7.57 (s, 2H). m/z (EI): 594 [M$^+$].

PREPARATION EXAMPLE 54

Synthesis of 4-(tert-Butyldimethylsilyloxymethyl)-imidazole

4-Hydroxymethylimidazole hydrochloride (5.03 g) was dissolved in a mixed solvent of dichloromethane (90 mL) and DMF (20 mL), and to the solution triethylamine (8.25 g) was added at 0° C. tert-Butyldimethylchlorosilane (6.14 g) was then added to the mixture, and the resultant mixture was stirred at room temperature. The reaction mixture was concentrated under reduced pressure, and the residue was diluted with ethyl acetate, washed with water and saturated brine, dried over anhydrous sodium sulfate and concentrated under reduced pressure. The residue was then purified by column chromatography on silica gel (chloroform:methanol=20:1) to obtain the title compound.

Yield: 6.21 g (79%). $^1$H-NMR (400 MHz, CDCl$_3$) δ: 0.08 (s, 6H), 0.91 (s, 9H), 4.73 (s, 2H), 6. 94 (s, 1H), 7.59 (s, 1H).

PREPARATION EXAMPLE 55

Synthesis of 4-(tert-Butyldimethylsilyloxymethyl)-1-(3,4,5-trimethoxyphenyl)imidazole 3,4,5-Trimethoxyphenylboronic acid (1.56 g) and 4-(tert-butyldimethylsilyloxymethyl)imidazole (1.26 g) were dissolved in dichloromethane (10 mL), and to the solution pyridine (562 mg) was added. Bisacetoxycopper (1.29 g) was then added to the mixture, and the mixture was stirred overnight at room temperature under an argon atmosphere. The reaction mixture was concentrated under reduced pressure, and the residue was diluted with ethyl acetate, washed with water and saturated brine, dried over anhydrous sodium sulfate and concentrated under reduced pressure. The residue was purified by column chromatography on silica gel (chloroform:methanol=50:1) to obtain the title compound.

Yield: 406 mg (18%). $^1$H-NMR (400 MHz, CDCl$_3$) δ: 0.14 (s, 6H), 0.95 (s, 9H), 3.87 (s, 3H), 3.90 (s, 6H), 4.76 (s, 2H), 6.57 (s, 2H), 7.14 (s, 1H), 7.71 (s, 1H).

PREPARATION EXAMPLE 56

Synthesis of 4-Hydroxymethyl-1-(3,4,5-trimethoxyphenyl)imidazole 4-(tert-Butyldimethylsilyloxymethyl)-1-(3,4,5-trimethoxyphenyl)imidazole (406 mg) was treated in the same manner as in Preparation Example 49 to obtain the title compound.

Yield: 194 mg (69%). $^1$H-NMR (400 MHz, CDCl$_3$) δ: 2.42 (br, 1H), 3.87 (s, 3H), 3.90 (s, 6H), 4.68 (s, 2H), 6.57 (s, 2H), 7.21 (br, 1H), 7.77 (br, 1H).

PREPARATION EXAMPLE 57

Synthesis of 4-Chloromethyl-1-(3,4,5-trimethoxyphenyl)imidazole

4-Hydroxymethyl-1-(3,4,5-trimethoxyphenyl)imidazole (190 mg) was treated in the same manner as in Preparation Example 4 to obtain the title compound.

Yield: 174 mg (86%). $^1$H-NMR (400 MHz, CDCl$_3$) δ: 3.87 (s, 3H), 3.90 (s, 6H), 4.65 (s, 2H), 6.56 (s, 2H), 7.26 (s, 1H), 7.75 (d, 1H, J=1.3 Hz).

EXAMPLE 26

Synthesis of N,N'-bis[[1-(3,4,5-Trimethoxyphenyl)imidazol-4-yl]methyl]piperazine 4-Chloromethyl-1-(3,4,5-trimethoxyphenyl)imidazole (87 mg) and piperazine (13 mg) were reacted in the same manner in Example 1 to obtain the title compound as a free base.

Yield: 21 mg (25%). $^1$H-NMR (400 MHz, CDCl$_3$) δ: 2.68 (br, 8H), 3.60 (s, 4H), 3.87 (s, 6H), 3.90 (s, 12H), 6.56 (s, 4H), 7.15 (s, 2H), 7.71 (s, 2H). m/z (EI): 578 [M$^+$].

PREPARATION EXAMPLE 58

Synthesis of 5-(3,4,5-Trimethoxyphenyl)thiophene-2-carboaldehyde 3,4,5-Trimethoxyphenylboronic acid (848 mg) and 5-chlorothiophene-2-carboaldehyde (764 mg) were suspended in a mixed solvent of toluene (20 mL) and THF (15 mL), and to the suspension 2 M sodium carbonate (8 mL) was added. Tetrakis(triphenylphosphine)palladium(0) (231 mg) was added to the mixture under an argon atmosphere, and the mixture was stirred at 90° C. for 5 hours as it is. After allowing the reaction mixture to cool, ethyl acetate was added to the reaction mixture to separate an organic layer. The organic layer was washed with saturated brine, dried over anhydrous sodium sulfate and concentrated under reduced pressure. The residue was purified by column chromatography on silica gel (hexane:ethyl acetate=5:1) to obtain the title compound.

Yield: 662 mg (60%).

PREPARATION EXAMPLE 59

Synthesis of 2-Hydroxymethyl-5-(3,4,5-trimethoxyphenyl)thiophene 5-(3,4,5-Trimethoxyphenyl)thiophene-2-carboaldehyde (662 mg) was dissolved in methanol (50 mL), and to the solution sodium borohydride (180 mg) was gradually added under ice cooling. After stirring the mixture at room temperature for 1 hour, the reaction mixture was concentrated under reduced pressure, and the residue was dissolved in chloroform. The resultant organic layer was washed with water and saturated brine, dried over anhydrous magnesium sulfate and concentrated under reduced pressure. The residue was purified by column chromatography on silica gel (hexane:ethyl acetate=3:1 to 2:1) to obtain the title compound.

Yield: 515 mg (77%). $^1$H-NMR (400 MHz, CDCl$_3$) δ: 1.52 (s, 1H), 3.87 (s, 3H), 3.91 (s, 6H), 4.83 (d, 2H, J=6.6 Hz), 6.78 (s, 2H), 6.97 (d, 1H, J=3.3 Hz), 7.10 (d, 1H, J=3.3 Hz).

EXAMPLE 27

Synthesis of N,N'-bis[[5-(3,4,5-Trimethoxyphenyl)-thiophen-2-yl]methyl]piperazine Dimaleate

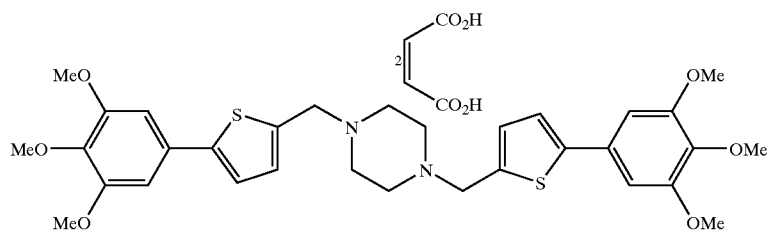

2-Hydroxymethyl-5-(3,4,5-trimethoxyphenyl)thiophene (234 mg) was treated in the same manner in Preparation Example 4 to synthesize 2-chloromethyl-5-(3,4,5-trimethoxyphenyl)thiophene. Since this product was unstable, it was immediately reacted with piperazine (36 mg) in the same manner in Example 1 without isolating it to obtain a product as a free base. This product was dissolved in methanol, and maleic acid was added to the solution, thereby converting it into the title compound.

Yield: 191 mg (54%). $^1$H-NMR (400 MHz, DMSO-d$_6$, 120° C.) δ: 2.89 (s, 8H), 3.75 (s, 6H), 3.85 (s, 12H), 4.04 (s, 4H), 6.14 (s, 4H), 6.73 (s, 4H), 7.03 (d, 2H, J=3.7 Hz), 7.25 (d, 2H, J=3.7 Hz). m/z (EI): 610 [M$^+$].

EXAMPLE 28

Synthesis of N,N'-bis[[5-(3,4,5-Trimethoxyphenyl)-thiophen-2-yl]methyl]homopiperazine Dimaleate

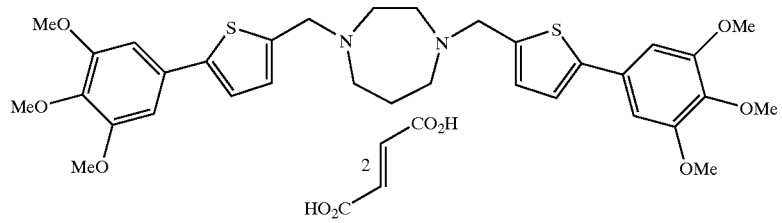

2-Hydroxymethyl-5-(3,4,5-trimethoxyphenyl)thiophene (230 mg) was treated in the same manner in Preparation Example 4 to synthesize 2-chloromethyl-5-(3,4,5-trimethoxyphenyl)thiophene. Since this product was unstable, it was immediately reacted with homopiperazine (41 mg) in the same manner in Example 1 without isolating it to obtain a product as a free base. This product was dissolved in methanol, and fumaric acid was added to the solution, thereby converting it into the title compound.

Yield: 44 mg (13%). $^1$H-NMR (400 MHz, DMSO-d$_6$, 120° C.) δ: 1.77 (q, 2H, J=6.1 Hz), 2.76 (s, 4H), 2.79 (t, 4H, J=6.1 Hz), 3.72 (s, 6H), 3.83 (s, 12H), 3.85 (s, 4H), 6.62 (s, 4H), 6.82 (s, 4H), 6.89 (d, 2H, J=3.7 Hz), 7.19 (d, 2H, J=3.7 Hz). m/z (EI): 624 [M$^+$].

TEST EXAMPLE

Inhibitory Effect on Cell Adhesion

This test was conducted by reference to the method of Ross et al. (J. Biol. Chem., 267, 8537–8543 (1992)). More specifically, after human umbilical venous endothelial cells (HUVEC) were cultured on a 48-well plate to confluent growth, IL-1β or TNFα was added thereto. Upon elapsed time of 5 hours after the addition, U937, which is a human monocytic/histocytic cell fluorescence-labeled with PKH2 (product of Dainippon Pharmaceutical Co., Ltd.), was added in a proportion of 1×10$^6$ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K.K.) and 10% FCS-containing RPMI1640, respectively. Each test agent was added to HUVEC upon the addition of IL-1β or TNFα and to U937 24 hours prior to the cell adhesion test. The inhibitory activity was calculated out according to the equation [100-(C−B)/(A−B)×100 (%)], wherein A is the number of U937 cells adhered to HUVEC stimulated by IL-1β or TNFα when no test agent was added, B is the number of U937 cells adhered to HUVEC not stimulated by IL-1β or TNFα when no test agent was added, and C is the number of U937 cells adhered to HUVEC stimulated by IL-1β or TNFα when the test agent was added. The results are shown in Table 1. As control compounds, Test Compound 1 described in Japanese Patent Application Laid-Open No. 9-143075 and dilazep described in Japanese Patent Application Laid-Open No. 11-92382 were simultaneously evaluated.

TABLE 1

Inhibitory activity of each compound at 1 μM against cell adhesion

| Example | Percent inhibition (%) | |
|---|---|---|
| | Stimulation by TNFα | Stimulation by IL-1β |
| 6 | 45 | 54 |
| 7 | 60 | 46 |
| 8 | 58 | 64 |
| 9 | 50 | 40 |
| 11 | 53 | 33 |
| 16 | 51 | 30 |
| Test compound 1 | 5 | 10 |
| Dilazep | 12 | 0 |

Specific formulation examples will hereinafter be described.

| Preparation Example 60 (Capsule preparation) | |
|---|---|
| N,N'-Bis[[2-(3,4,5-trimethoxybenzamido)-thiazol-4-yl]methyl]piperazine- | 30 mg |
| Microcrystalline cellulose | 30 mg |
| Lactose | 57 mg |
| Magnesium stearate | 3 mg |
| Total amount | 120 mg. |

The above ingredients were mixed in accordance with a method known per se in the art and then charged in a gelatin capsule to obtain a capsule preparation.

| Preparation Example 61: (Tablet preparation) | |
|---|---|
| N,N'-Bis[[2-(3,4,5-trimethoxybenzamido)-thiazol-4-yl]methyl]piperazine- | 30 mg |
| Starch | 44 mg |
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain a tablet preparation.

PREPARATION EXAMPLE 61

Injection Preparation

N,N'-Bis[[2-(3,4,5-trimethoxybenzamido)thiazol-4-yl]methyl]piperazine (100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 light-screening ampoules, and the ampoules were sealed to obtain injection preparations.

As described above, the compounds (1) according to the present invention have inhibitory effects on both cell adhesion and cell infiltration and are useful as medicines for prevention or treatment of diseases such as allergy, asthma, rheumatism, arteriosclerosis and inflammation.

Obviously, numerous modifications of the above teachings are apparent to those skilled in the art. Therefore, within the scope of the appended claims, the invention may be practiced otherwise than as specifically described herein.

What is claimed is:

1. A compound of formula (1):

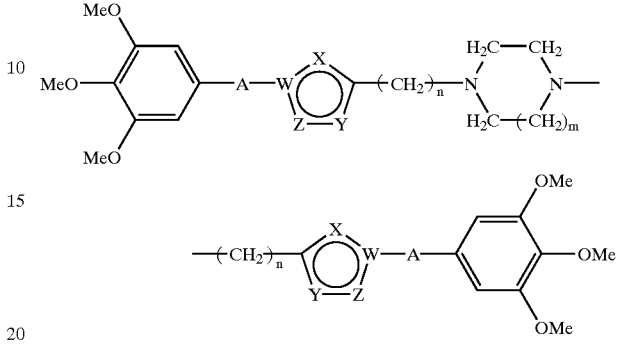

(I)

wherein A is a single bond, C≡C, CONH or NHCO; W is a carbon atom or a nitrogen atom; X is CH, a nitrogen atom, an oxygen atom or a sulfur atom; Y is CH, CHR$^1$, in which R$^1$ is a hydrogen atom, or a lower alkyl, hydroxy lower alkyl, lower alkoxy-lower-alkyl, aryl, aryl-lower-alkyl or heteroaryl-lower-alkyl group, a nitrogen atom, an oxygen atom, a sulfur atom or NR$^2$, in which R$^2$ is a hydrogen atom, or a lower alkyl, hydroxy lower alkyl, lower alkoxy-lower-alkyl, aryl, aryl-lower-alkyl or heteroaryl-lower-alkyl group; Z is a nitrogen atom, an oxygen atom, a sulfur atom, CH or NR$^3$, in which R$^3$ is a hydrogen atom, or a lower alkyl, hydroxy lower alkyl, lower alkoxy-lower-alkyl, aryl, aryl-lower-alkyl or heteroaryl-lower-alkyl group; m is 1 or 2; and n is a number of 1 to 5, with the proviso that one or two of W, X, Y and Z are heteroatoms;

an acid-addition salt thereof, or a hydrate thereof.

2. The compound of claim 1, wherein R$^1$, R$^2$ and R$^3$ are individually a hydrogen atom, C$_1$–C$_6$-alkyl group, hydroxy-C$_2$–C$_6$-alkyl group, C$_1$–C$_6$-alkoxy-C$_1$–C$_6$-alkyl group, C$_6$–C$_{10}$-aryl, C$_6$–C$_{10}$-aryl-C$_1$–C$_6$-alkyl group or pyridyl-C$_1$–C$_6$-alkyl group.

3. The compound of claim 1, wherein a heterocycle constituting the moiety

is a heterocycle selected from the group consisting of thiazole, oxazole, imidazole, pyrazole, isothiazole, isoxazole, pyrrole, thiophene and furan.

4. A pharmaceutical composition comprising, as an active ingredient, a compound of formula (1):

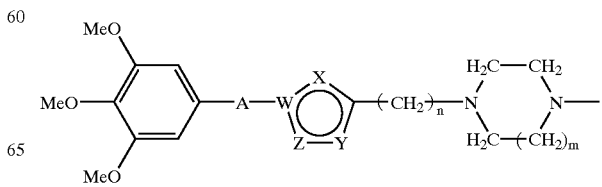

(I)

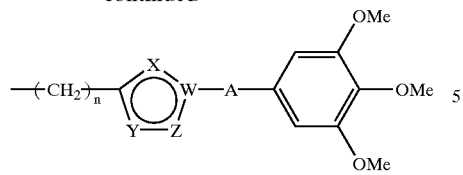

wherein A is a single bond, C≡C, CONH or NHCO; W is a carbon atom or a nitrogen atom; X is CH, a nitrogen atom, an oxygen atom or a sulfur atom; Y is CH, CHR$^1$, in which R$^1$ is a hydrogen atom, or a lower alkyl, hydroxy lower alkyl, lower alkoxy-lower-alkyl, aryl, aryl-lower-alkyl or heteroaryl-lower-alkyl group, a nitrogen atom, an oxygen atom, a sulfur atom or NR$^2$, in which R$^2$ is a hydrogen atom, or a lower alkyl, hydroxy lower alkyl, lower alkoxy-lower-alkyl, aryl, aryl-lower-alkyl or heteroaryl-lower-alkyl group; Z is a nitrogen atom, an oxygen atom, a sulfur atom, CH or NR$^3$, in which R$^3$ is a hydrogen atom, or a lower alkyl, hydroxy lower alkyl, lower alkoxy-lower-alkyl, aryl, aryl-lower-alkyl or heteroaryl-lower-alkyl group; m is 1 or 2; and n is a number of 1 to 5, with the proviso that one or two of W, X, Y and Z are heteroatoms;

an acid-addition salt thereof, or a hydrate thereof, and a pharmaceutically acceptable carrier.

5. The pharmaceutical composition of claim 4, wherein R$^1$, R$^2$ and R$^3$ are individually a hydrogen atom, C$_1$–C$_6$-alkyl group, hydroxy-C$_2$–C$_6$-alkyl group, C$_1$–C$_6$-alkoxy-C$_1$–C$_6$-alkyl group, C$_6$–C$_{10}$-aryl, C$_6$–C$_{10}$-aryl-C$_1$–C$_6$-alkyl group or pyridyl-C$_1$–C$_6$-alkyl group.

6. The pharmaceutical composition of claim 4, wherein a heterocycle constituting the moiety

is a heterocycle selected from the group consisting of thiazole, oxazole, imidazole, pyrazole, isothiazole, isoxazole, pyrrole, thiophene and furan.

7. The pharmaceutical composition of claim 4, which comprises an agent for treating a disease caused by cell adhesion and/or cell infiltration.

8. The pharmaceutical composition of claim 7, wherein the disease is selected from the group consisting of allergy, asthma, inflammation, rheumatism and arteriosclerosis.

9. A method for treating a disease caused by cell adhesion and/or cell infiltration, wherein said disease is allergy, asthma, inflammation, rheumatism, and arteriosclerosis, which comprises administering to a patient in need thereof an effective amount of a compound of formula (1):

(I)

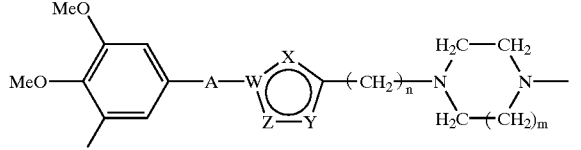

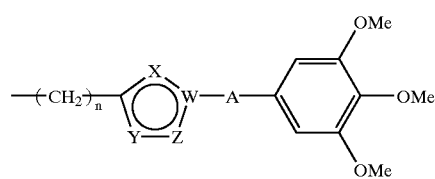

wherein A is a single bond, C≡C, CONH or NHCO; W is a carbon atom or a nitrogen atom; X is CH, a nitrogen atom, an oxygen atom or a sulfur atom; Y is CH, CHR$^1$, in which R$^1$ is a hydrogen atom, or a lower alkyl, hydroxy lower alkyl, lower alkoxy-lower-alkyl, aryl, aryl-lower-alkyl or heteroaryl-lower-alkyl group, a nitrogen atom, an oxygen atom, a sulfur atom or NR$^2$, in which R$^2$ is a hydrogen atom, or a lower alkyl, hydroxy lower alkyl, lower alkoxy-lower-alkyl, aryl, aryl-lower-alkyl or heteroaryl-lower-alkyl group; Z is a nitrogen atom, an oxygen atom, a sulfur atom, CH or NR$^3$, in which R$^3$ is a hydrogen atom, or a lower alkyl, hydroxy lower alkyl, lower alkoxy-lower-alkyl, aryl, aryl-lower-alkyl or heteroaryl-lower-alkyl group; m is 1 or 2; and n is a number of 1 to 5, with the proviso that one or two of W, X, Y and Z are heteroatoms; an acid-addition salt thereof, or a hydrate thereof.

10. The method according to claim 9, wherein said disease caused by cell adhesion and/or cell infiltration is allergy.

11. The method according to claim 9, wherein said disease caused by cell adhesion and/or cell infiltration is asthma.

12. The method according to claim 9, wherein said disease caused by cell adhesion and/or cell infiltration is inflammation.

13. The method according to claim 9, wherein said disease caused by cell adhesion and/or cell infiltration is rheumatism.

14. The method according to claim 9, wherein said disease caused by cell adhesion and/or cell infiltration is arteriosclerosis.

* * * * *